(12) United States Patent
Franaszczuk et al.

(10) Patent No.: US 10,031,105 B2
(45) Date of Patent: Jul. 24, 2018

(54) ELECTROCHEMICAL TOTAL ORGANIC CARBON ANALYZER

(71) Applicant: General Electric Company, Schenectady, NY (US)

(72) Inventors: Krzystof Franaszczuk, Boulder, CO (US); Mariem-Ruth Rosario-Canales, Trevose, PA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 509 days.

(21) Appl. No.: 14/400,689

(22) PCT Filed: Dec. 14, 2012

(86) PCT No.: PCT/US2012/069706
§ 371 (c)(1),
(2) Date: Nov. 12, 2014

(87) PCT Pub. No.: WO2013/172868
PCT Pub. Date: Nov. 21, 2013

(65) Prior Publication Data
US 2015/0129435 A1    May 14, 2015

Related U.S. Application Data

(60) Provisional application No. 61/647,335, filed on May 15, 2012.

(51) Int. Cl.
*G01N 27/49* (2006.01)
*G01N 33/00* (2006.01)
(Continued)

(52) U.S. Cl.
CPC ........... *G01N 27/49* (2013.01); *G01N 33/004* (2013.01); *G01N 33/1846* (2013.01); *G01N 27/4045* (2013.01)

(58) Field of Classification Search
CPC ............. G01N 27/4045; G01N 33/004; G01N 33/0011; G01N 33/0013
See application file for complete search history.

(56) References Cited

U.S. PATENT DOCUMENTS 4,729,824 A    3/1988 Giner
4,824,551 A    4/1989 Rupich
(Continued)

FOREIGN PATENT DOCUMENTS

DE    102008010581 A1    8/2009
EP    0 659 691    6/1995
(Continued)

OTHER PUBLICATIONS

Hunter et al., "Miniaturized Amperometric Solid Electrolyte Carbon Dioxide Sensors," Electrochemical Society Transactions, 3(10) 203-211 (2006).*

(Continued)

*Primary Examiner* — Alexander S Noguerola
(74) *Attorney, Agent, or Firm* — Wegman, Hessler & Vanderburg

(57) ABSTRACT

An apparatus is disclosed for measuring the total organic content of an aqueous stream. The apparatus comprises a platinum electrode for measuring $CO_2$ in an aqueous stream. Methods for measuring the total organic content of an aqueous stream are also disclosed. The methods comprise providing an aqueous stream with oxidized organics therein; providing a platinum electrode, contacting the aqueous stream with the platinum electrode; applying cathodic potential followed by an anodic voltammetric sweep to the platinum electrode, and measuring the amperometric response of the platinum electrode. An apparatus for oxidizing organics in aqueous stream in an aqueous stream is also disclosed.

38 Claims, 23 Drawing Sheets

(51) Int. Cl.
*G01N 33/18* (2006.01)
*G01N 27/404* (2006.01)

(56) References Cited

U.S. PATENT DOCUMENTS

| | | | |
|---|---|---|---|
| 5,399,247 | A | 3/1995 | Carey et al. |
| 6,106,692 | A | 8/2000 | Kunimatsu et al. |
| 6,267,866 | B1 | 7/2001 | Glesener et al. |
| 7,632,393 | B2 | 12/2009 | Kounaves |
| 2010/0267160 | A1 | 10/2010 | Erickson et al. |
| 2010/0294672 | A1 | 11/2010 | Gahr et al. |

FOREIGN PATENT DOCUMENTS

| | | | | |
|---|---|---|---|---|
| GB | 2382138 | A * | 5/2003 | ............ G01N 33/18 |
| JP | S59500833 | A | 5/1984 | |
| JP | 2007155671 | A | 6/2007 | |
| WO | 9721096 | A1 | 6/1997 | |

OTHER PUBLICATIONS

JPO computer-generated English language translation of JP07-299467A, downloaded from the JPO website on Mar. 28, 2017.*

EPO computer-generated English language translation of DE102008010581 A1 downloaded on Mar. 28, 2017.*

Iwaki et al., "Electrical Conductivity of Nitrogen and Argon Implanted Diamond", Nuclear Instruments and Methods, pp. 1129-1133, 1983.

Dixon et al., "Th Control and Measurement of 'CO2' During Fermentations", Journal of MicroBiological Methods, vol. No. 10, Issue No. 3, pp. 155-176, Nov. 1, 1989.

Millet et al., "Precipitation of Metallic Platinum into Nafion Ionomer Membranes", Electrochemical Society, pp. 1373-1380, 1993.

Parpot et al., "Electrocatalytic Oxidation of Sucrose:analysis of the Reaction Products", Applied Electrochemistry, pp. 25-33, 1997.

Taniguchi et al., "Catalytic Electrodes for Sensing Sugars", Chemical Sensors, vol. No. 18, pp. 100-102, 2002.

Marselli, "Electrochemical Oxygen Transfer Reaction on Synthetic Boron-Doped Diamond Thin Film Electrode", Ecole Polytechnique Federale de Lausanne, 2004.

CSEM, "Diamonds and State-of-the-art Technologies for Pure Water", CSEM Presents Innovative Environmental Systems, pp. 1-2, 2005.

Wang et al., "Solid Polymer Electrolyte-Based CO2 Sensor Using Anodic Adsorbate Stripping", Analytical Letters, vol. No. 38, Issue No. 13, pp. 2057-2065, Jan. 1, 2008.

Photinon et al., "Thick Film Carbon Dioxide Sensor via Anodic Adsorbate Stripping Technique and its Structural Dependence", Sensors, vol. No. 9, Issue No. 9, Jan. 1, 2009.

PCT Search Report and Written Opinion issued in connection with corresponding PCT Application No. PCT/US2012/069706 dated May 13, 2013.

9210e Online TOC Analyzer, as seen on http://www.oico.com/default.aspx?id=product&productID=121 as on Aug. 31, 2013, retrieved through web archive on Aug. 3, 2015.

Unofficial English Translation of Chinese Office Action issued in connection with corresponding CN Application No. 201280073201.3 dated Sep. 2, 2015.

Unofficial English Translation of Japanese Search Report issued in connection with corresponding JP Application No. 2015-512618 dated Oct. 14, 2016.

Unofficial English Translation of Japanese Office Action issued in connection with corresponding JP Application No. 2015-512618 dated Nov. 8, 2016.

Unofficial English Translation of Chinese Office Action issued in connection with corresponding CN Application No. 201280073201.3 dated Nov. 24, 2016.

Unofficial English Translation of Chinese Office Action issued in connection with corresponding CN Application No. 201280073201.3 dated May 5, 2016.

* cited by examiner

ELECTROCHEMICAL TOTAL ORGANIC CARBON ANALYZER

FIELD OF THE INVENTION

The invention relates to the field of determining the concentration of organic contaminants in a water sample matrix by measuring total organic carbon (TOC) using electrochemical oxidation and detection methods.

BACKGROUND OF THE INVENTION

Water quality is often indicated by the total organic carbon (TOC) present in the sample. Total organic carbon (TOC) is a well-established water quality parameter that quantifies the overall concentration of organic substances, all of which are typically regarded as contaminants. In most aqueous samples, such as drinking water, raw water, wastewater, industrial process streams, and the like, the total carbon (TC) is the sum of the amount of total organic carbon (TOC) and the amount of inorganic carbon (IC) present in the sample.

Most TOC measurement techniques involve 3 steps: first, measure the concentration of inorganic carbon (i.e. carbon in all the forms of dissolved carbon dioxide); second, oxidize organics in sample water to $CO_2$; and third, measure the $CO_2$ derived from the organics. Some instruments, however, allow for the acidification of the sample and purge $CO_2$ so that the inorganic carbon (IC) concentration is not measured. Oxidation of the organics in the water sample is traditionally achieved by UV radiation (with or without a chemical oxidizer present), combustion, or heat treatment (with or without catalysts or oxidizing agents). Mercury vapor lamps used in UV radiation cause harmful radiation and have a short service life. UV-persulfate oxidation adds harmful chemical oxidants.

Use of electrochemical methods has become an attractive alternative to traditional methods for treating water that contains dissolved organic compounds. Generally, organic pollutants dissolved in the water can be destroyed electrochemically by direct anodic oxidation at the electrode surface or indirectly through oxidation processes mediated by electrogenerated oxidants. The compound's oxidation potential and the choice of electrode material both influence where oxidation is by direct or indirect means. Classical electrode materials like platinum tend to suffer from several problems when used during electrolytic oxidation. Slow reaction rates, low efficiencies, and deactivation of the surface are possible. Corrosion during anodic polarization may also occur. Platinum offers a limited anodic range making direct organic oxidation problematic.

Conventional methods to measure inorganic carbon ($CO_2$, $H_2CO_3$, $HCO_3^-$, and $CO_3^{2-}$) and the $CO_2$ obtained from oxidation of the organics include conductivity measurements, infrared absorbance photometry, reaction of $CO_2$ with a colored indicator and measurement of the intensity of that color or $CO_2$ conversion to another species followed by flame ionization detection.

Conductivity detectors measure $CO_2$ in the water sample and may be divided into two groups: direct and membrane-based conductivity. The direct conductivity method is susceptible to interference from the ionic content of water from other sources besides $CO_2$. In the membrane-based conductometric method, a $CO_2$— permeable membrane is located between the sample water chamber and the deionized water acceptor chamber to separate the $CO_2$ from the sample matrix. The membrane selectively passes only $CO_2$ and serves as a protective barrier to interfering substances in the liquid.

Most TOC analyzers that operate based on combustion oxidation and conventional measurement techniques are typically, large, complex, and costly instruments. Many TOC analyzers are laboratory units. These units are not portable or suitable for "field use", wherein the instruments are brought to the water system being tested and are used to test the system for a short period of time. Instead, samples must be brought to the analyzer for testing in a controlled environment. Many TOC analyzers are not easily adapted to an "on-line" system wherein the instrument is placed in the water system being tested and aqueous samples may be tested and monitored automatically, without human intervention.

TOC analyzers may also be classified as "flow-through" or "batch" instruments. The term "flow-through" is used to describe an instrument wherein the samples are flowing samples streams as opposed to "batch" wherein the samples are collected and analyzed. In flow-through instruments, the sample may flow continuously through the instrument as it is analyzed and may be returned to the sample source or directed elsewhere for treatment or disposal. Many flow-through instruments, however, may also have an auto sampler wherein the samples are collected and analyzed, allowing the instrument to operate as a batch instrument.

BRIEF DESCRIPTION OF THE INVENTION

Accordingly, methods, apparatuses, and systems are disclosed that are not only suitable for laboratory use, but are also suitable for portable, on-line, or flow-through applications. In one embodiment, a method for measuring carbon dioxide in an aqueous stream is disclosed. The method may comprise providing an aqueous stream, wherein any organic carbon has been oxidized therein and providing a carbon dioxide measurement module comprising at least one platinum electrode therein. The aqueous stream may be contacted with the platinum electrode. A cathodic potential followed by an anodic potential may be applied to the platinum electrode while maintaining contact of the platinum electrode with the aqueous stream. The amperometric response of the platinum may be measured and equated to a total organic carbon content of the aqueous stream. In another embodiment, the anodic potential may be an anodic potential sweep or an anodic potential step. In another embodiment, the platinum electrode may be platinized. Alternatively, the platinum electrode may be decorated with gold adatoms. In yet another embodiment, the organic carbon in the aqueous stream may be oxidized using a method selected from the group consisting of electrooxidation, chemical oxidation, UV-persulfate oxidation, thermal oxidation, and catalytic oxidation. In another embodiment, the method may further comprise adding an electrolyte to the aqueous stream before applying the cathodic potential to the platinum electrode. In yet another embodiment, the electrolyte may comprise an acid, such as sulfuric acid.

In yet another method embodiment, the total organic carbon in an aqueous stream may be measured. The method may comprise providing an aqueous stream, providing an oxidation module comprising at least one doped diamond electrode therein, and providing a carbon dioxide measurement module comprising at least one platinum electrode therein. The method may comprise contacting the aqueous stream with the doped diamond electrode in the oxidation module and applying an oxidizing potential to the doped diamond electrode to oxidize any organics in the aqueous stream and form an oxidized aqueous stream. The oxidized aqueous stream may then be transferred from the oxidation module to the carbon dioxide measurement module. The method may also comprise contacting the oxidized aqueous stream with the platinum electrode and applying a cathodic potential followed by applying an anodic potential to the platinum electrode. The method may also comprise measuring an amperometric response of the platinum electrode and equating the amperometric response of the platinum electrode to a total organic content of the aqueous stream. In another embodiment, a method is disclosed wherein the platinum electrode may be platinized. Alternatively, the platinum electrode may be decorated with gold adatoms. In yet another embodiment, the doped diamond electrode may be a boron-doped diamond electrode. In another embodiment, the method may further comprise adding an electrolyte to the aqueous stream or the oxidized aqueous stream before applying the cathodic potential to the platinum electrode. In yet another method embodiment, the electrolyte may comprise an acid, such as sulfuric acid. In another method the anodic potential may be an anodic potential sweep or an anodic potential step. In yet another embodiment, the oxidizing potential may be a static anodic potential, an alternating potential waveform, or anodic potential pulses.

In another embodiment, an apparatus for oxidizing organics in an aqueous stream is disclosed. The apparatus may comprise an oxidizing module comprising a dual-compartment cell therein. The dual-compartment cells may have a first compartment with a doped diamond anode therein and a second compartment with a cathode therein. The oxidation module may be configured to contact the aqueous stream with the doped diamond electrode and to apply an oxidizing potential to the doped-diamond anode, thereby oxidizing any organics in the aqueous stream to form an oxidized aqueous stream. In another embodiment, the dual-compartment cell may further comprise a conducting membrane separating the first and second compartments. The conducting membrane may be a proton exchange membrane. In yet another embodiment, the oxidizing potential may be a static anodic potential, an alternating potential waveform, or anodic potential pulses. In another embodiment, the doped diamond anode may be a boron-doped diamond anode.

In another embodiment, an apparatus for measuring total organic carbon in an aqueous stream is disclosed. The apparatus may comprise an oxidation module comprising at least one doped diamond electrode therein. The oxidation module may be configured to contact the aqueous stream with the doped diamond electrode and to apply an oxidizing potential to the doped diamond electrode thereby oxidizing any organics in the aqueous stream to form an oxidized aqueous stream. The apparatus may also comprise a carbon dioxide measurement module comprising at least one platinum electrode therein. The carbon dioxide measurement module may be configured to contact the oxidized aqueous stream with the platinum electrode and to apply a cathodic potential and thereafter apply an anodic potential to the platinum electrode. The apparatus may also comprise a fluid transfer module operatively connected to the oxidation module and the carbon dioxide measurement module and configured to transfer the oxidized aqueous stream from the oxidation module to the carbon dioxide measurement module. The apparatus may also comprise a control module operatively connected to the carbon dioxide measurement module and configured to measure an amperometric response of the platinum electrode and to equate the amperometric response of the platinum electrode to a total organic content of the aqueous stream. In yet another embodiment, the control module may be further operatively connected to the oxidation module and the fluid transfer module. In another embodiment of the apparatus, the platinum electrode may be platinized. Alternatively, the platinum electrode may be decorated with gold adatoms. In another embodiment, the doped diamond electrode may be a boron-doped diamond electrode. In another embodiment, the anodic potential may be an anodic potential sweep or an anodic potential step. The oxidizing potential may be a static anodic potential, an alternating potential waveform, or anodic potential pulses. In yet another embodiment, the oxidation module may further comprise a dual-compartment cell, wherein the dual-compartment cell has a first compartment with an anode therein and a second compartment with a cathode therein. In another embodiment, the dual-compartment cell may further comprise a conducting membrane that separates the first compartment from the second compartment. The conducting membrane may be a proton exchange membrane.

In another embodiment, a system for measuring carbon dioxide an aqueous stream is disclosed. The system may comprise a memory and a processor operatively connected to the memory. The processor may be configured to receive inputs, such as an amperometric response of a platinum electrode, and use the inputs to generate outputs, such as a total organic content of an aqueous stream. The processor may be further configured to store the outputs in the memory. The inputs comprising an amperometric response may be generated by contacting an aqueous stream with a platinum electrode, applying a cathodic potential to the platinum electrode and then applying an anodic potential to the platinum electrode while maintaining contact with the aqueous stream. In another system embodiment, the platinum electrode may be platinized. Alternatively, the platinum electrode may be decorated with gold adatoms. In yet another system embodiment, the inputs may further comprise a background amperometric response.

A non-transitory computer readable medium with computer executable instructions stored thereon executed by a processor to perform the method of measuring carbon dioxide in an aqueous stream is disclosed. The method including applying a cathodic potential to a platinum electrode contacting the aqueous stream, applying an anodic potential to the platinum electrode, measuring the amperometric response of the platinum electrode, calculating a total organic carbon content of the aqueous stream using the measured amperometric response, and storing the calculated total organic carbon content in the memory. The method can also include measuring a background amperometric response, wherein the total organic carbon content of the aqueous stream is calculated using the measured amperometric response and the measured background amperometric response.

DETAILED DESCRIPTION OF EXEMPLARY EMBODIMENTS

Figure 1:
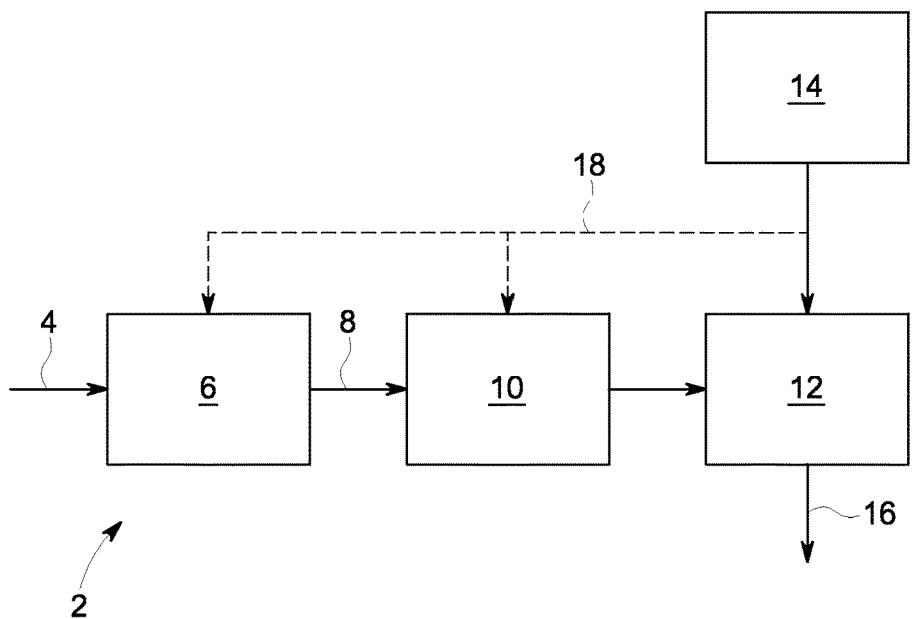
FIG. 1 shows an embodiment of a total organic carbon analyzer.

Methods, apparatuses, and systems are disclosed that are not only suitable for laboratory use, but are also suitable for portable, on-line, or flow-through applications. The invention relates to determining the total concentration of organic contaminants in water by measuring total organic carbon (TOC) using electrochemical methods. The invention may comprise a carbon electrooxidation scheme, a $CO_2$ electrochemical measurement scheme, or a combination of the two schemes.

The principle behind an electrochemical approach to $CO_2$ electrochemical measurements lies in the physicochemical properties of carbon:

Carbon atoms can easily change oxidation stage by exchanging electrons with electrodes;

Carbon at its highest oxidation stage (+4) forms exclusively carbon dioxide;

Carbon dioxide exhibits no specific adsorption on variety of catalytic metals; and Carbon at lower oxidation stages (+2 in carbon monoxide, but not limited to it) chemisorbs on most catalytic materials (this process is often referred to as poisoning).

The disclosed TOC measurements comprise three separate steps in which carbon undergoes electrocatalytic reactions. The first step transforms all organic carbon to carbon dioxide in a heterogeneous oxidation step. This step is demonstrated in Example Set 1. The second step performs two tasks: reduce carbon dioxide to carbon monoxide; and concentrate carbon monoxide on the surface of the electrode. The third step, like the first step, is an oxidation reaction. The second and third steps are demonstrated in Example Set 2.

As noted above, the first and third steps are oxidation steps. The oxidation in the third step, however, takes place in a different environment than in the first step. In the third step, carbon monoxide adsorbed on the platinum electrode surface is oxidized to carbon dioxide in an anodic stripping process. Step three must occur in connection with step two. Since all substrate carbon is present as carbon monoxide chemisorbed at the electrode surface, there is a direct proportionality between electrical charge used in step three and TOC concentration.

The entire process comprising the above three steps may be described as electrooxidation, followed by chemisorption, followed by anodic stripping voltammetry.

In TOC measurements, electro-oxidation is performed first. The reaction is carried out in the conditions optimized for converting most of the analyte's carbon into carbon dioxide as in Formula I:

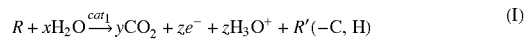

$$R + xH_2O \xrightarrow{cat_1} yCO_2 + ze^- + zH_3O^+ + R'(-C, H) \quad (I)$$

where R denotes organic carbon compounds, including but not limited to, isopropyl alcohol, methanol, and sucrose;
$cat_1$ is an electrode comprising a material including, but not limited to, boron doped diamond, nitrogen doped diamond, platinum; and
x, y, and z are stoichiometric values that may vary with R.

In the chemisorption step, reduction leads to the formation of the layer of chemisorbed carbon monoxide (often referred as catalyst poisoning) as in Formula II:

$$CO_2 + 2e^- + H_2O \xrightarrow{cat_2} CO_{ads} + 2OH^- \quad (II)$$

where $cat_2$ is an electrode material comprising platinum, gold, or a combination thereof. In the application presented here, the formation of irreversible platinum and chemisorbed carbon monoxide bonding may be used for concentrating carbon on the platinum surface.

Once chemisorbed carbon monoxide is formed, it can be quantified in the oxidation process. Unlike the initial oxidation process, the reoxidation process is fast and stoichiometric. All analyte is in the form of carbon monoxide and is already present on the reaction surface. Therefore, the kinetics of this process has no diffusion limitations as in Formula III.

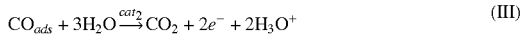

$$CO_{ads} + 3H_2O \xrightarrow{cat_2} CO_2 + 2e^- + 2H_3O^+ \quad (III)$$

When the CO is reoxidized, the electrical charge is measured. There is a straight forward correlation between the oxidation charge and carbon concentration based on the analyte's flow rate and the chemisorption step duration.

Accordingly, in one embodiment, a method for measuring carbon dioxide in an aqueous stream is disclosed. The method may comprise providing an aqueous stream, wherein any organic carbon has been oxidized therein and providing a carbon dioxide measurement module comprising at least one platinum electrode therein. The aqueous stream may be contacted with the platinum electrode. A cathodic potential followed by an anodic potential may be applied to the platinum electrode while maintaining contact of the platinum electrode with the aqueous stream. The amperometric response of the platinum may be measured and equated to a total organic carbon content of the aqueous stream. In another embodiment, the anodic potential may be an anodic potential sweep or an anodic potential step. In another embodiment, the platinum electrode may be platinized. Alternatively, the platinum electrode may be decorated with gold adatoms. Traditional oxidation methods well known in the art, such as UV-persulfate oxidation, may be combined with the $CO_2$ electrochemical measurement. Accordingly, in yet another embodiment, the organic carbon in the aqueous stream may be oxidized using a method selected from the group consisting of electrooxidation, chemical oxidation, UV-persulfate oxidation, thermal oxidation, and catalytic oxidation. In another embodiment, the method may further comprise adding an electrolyte to the aqueous stream before applying the cathodic potential to the platinum electrode. In yet another embodiment, the electrolyte may comprise an acid, such as sulfuric acid.

In yet another method embodiment, the total organic carbon in an aqueous stream may be measured. The method may comprise providing an aqueous stream, providing an oxidation module comprising at least one doped diamond electrode therein, and providing a carbon dioxide measurement module comprising at least one platinum electrode therein. The method may comprise contacting the aqueous stream with the doped diamond electrode in the oxidation module and applying an oxidizing potential to the doped diamond electrode to oxidize any organics in the aqueous stream and form an oxidized aqueous stream. The oxidized aqueous stream may then be transferred from the oxidation module to the carbon dioxide measurement module. The method may also comprise contacting the oxidized aqueous stream with the platinum electrode and applying a cathodic potential followed by applying an anodic potential to the platinum electrode. The method may also comprise measuring an amperometric response of the platinum electrode and equating the amperometric response of the platinum electrode to a total organic content of the aqueous stream. In another embodiment, a method is disclosed wherein the platinum electrode may be platinized. Alternatively, the platinum electrode may be decorated with gold adatoms. In yet another embodiment, the doped diamond electrode may be a boron-doped diamond electrode. In another method the anodic potential may be an anodic potential sweep or an anodic potential step. In yet another embodiment, the oxidizing potential may be a static anodic potential, an alternating potential waveform, or anodic potential pulses.

In another embodiment, the method may further comprise adding an electrolyte to the aqueous stream or the oxidized aqueous stream. Whether or not an electrolyte is required will depend on the application and the specific analyte being tested. Conductive analytes may not require an additional electrolyte. If the analyte is not sufficiently conductive, adding an electrolyte may improve the conductivity of the analyte, thereby allowing the $CO_2$ to be measured electrochemically. Accordingly, the electrolyte may be added to the oxidized aqueous stream before applying the cathodic potential to the platinum electrode. Any electrolyte is suitable, including solutions of acids, bases and salts. In cases where the electrolyte is sulfuric acid or hydrochloric acid, it may even improve the oxidation process. In the case of sulfuric acid, the sulfuric acid will oxidize to a peroxysulfuric acid (i.e. peroxymonosulfuric or peroxydisulfuric) when the oxidation potential is applied to the doped diamond electrode. Pesulfate ions act as oxidizing agents in many in-situ chemical oxidation applications, including UV light oxidation. Accordingly, the electrolyte may be added to the aqueous stream before the oxidation potential is applied. If the electrolyte is added before the oxidation step, additional electrolyte may not be required in the $CO_2$ measurement step. Thus, in another embodiment, the method may comprise adding an electrolyte to either the aqueous stream before applying said oxidation potential, or to the oxidized aqueous stream before applying said cathodic potential. In yet another method embodiment, the electrolyte may comprise an acid, such as sulfuric acid.

In another embodiment, an apparatus for oxidizing organics in an aqueous stream is disclosed. The apparatus may comprise an oxidizing module comprising a dual-compartment cell therein. The dual-compartment cells may have a first compartment with a doped diamond anode therein and a second compartment with a cathode therein. The oxidation module may be configured to contact the aqueous stream with the doped diamond electrode and to apply an oxidizing potential to the doped-diamond anode, thereby oxidizing any organics in the aqueous stream to form an oxidized aqueous stream. In another embodiment, the dual-compartment cell may further comprise a conducting membrane separating the first and second compartments. The conducting membrane may be a proton exchange membrane. In yet another embodiment, the oxidizing potential may be a static anodic potential, an alternating potential waveform, or anodic potential pulses. In another embodiment, the doped diamond anode may be a boron-doped diamond anode.

In another embodiment, an apparatus for measuring total organic carbon in an aqueous stream is disclosed. The apparatus may comprise two consecutive reaction modules. The first module, or "oxidation" module, may be an electrochemical cell with conditions optimized to convert the analyte's carbon to carbon dioxide by electrochemical oxidation. The second module, or "carbon dioxide measurement" module, may be an electrochemistry-based $CO_2$ sensor where the dissolved $CO_2$ produced is detected and quantified. The analyte, or sample, may be an aqueous stream. The analyte with carbon oxidized to $CO_2$ in the oxidation module is then fed to the carbon dioxide measurement module.

As shown in FIG. 1, the apparatus (2) may comprise an oxidation module (6) comprising at least one doped diamond electrode therein. The oxidation module may be configured to contact the aqueous stream (4) with the doped diamond electrode and to apply an oxidizing potential to the doped diamond electrode thereby oxidizing any organics in the aqueous stream to form an oxidized aqueous stream (8). The apparatus may also comprise a carbon dioxide measurement module (12) comprising at least one platinum electrode therein. The carbon dioxide measurement module may be configured to contact the oxidized aqueous stream with the platinum electrode and apply a cathodic potential to the platinum electrode and thereafter apply an anodic potential to the platinum electrode. The apparatus may also comprise a fluid transfer module (10) operatively connected to the oxidation module and the carbon dioxide measurement module and configured to transfer the oxidized aqueous stream from the oxidation module to the carbon dioxide measurement module. The fluid transfer module may comprise one or more fluid transfer components known to persons of ordinary skill in the art for assisting in transferring the aqueous stream. Such fluid transfer components include, but are not limited to, tubes, pipes, hoses, channels, valves, pumps, etc. The apparatus may also comprise a control module (14), operatively connected to the carbon dioxide measurement module and configured to measure an amperometric response of the platinum electrode and equating the amperometric response of the platinum electrode to a total organic content of the aqueous stream. Persons of ordinary skill in the art may recognize that the control module may also be operatively connected to the oxidation and the fluid transfer modules (18). The control module may comprise a programmable logic controller or similar device and an electronics unit used to control the function of the other modules it is operatively connected to, take measurements, collect data, and make calculations. Once the TOC of the aqueous stream has been measured, the aqueous stream (16) may leave the carbon dioxide measurement module. In another embodiment of the apparatus, the platinum electrode may be platinized. Alternatively, the platinum electrode may be decorated with gold adatoms. In another embodiment, the doped diamond electrode may be a boron-doped diamond electrode. In another embodiment, the anodic potential may be an anodic potential sweep or an anodic potential step. The oxidizing potential may be a static anodic potential, an alternating potential waveform, or anodic potential pulses. In yet another embodiment, the oxidation module may further comprise a dual-compartment cell, wherein the dual-compartment cell has a first compartment with an anode therein and a second compartment with a cathode therein. In another embodiment, the dual-compartment cell may further comprise a conducting membrane that separates the first compartment from the second compartment. The conducting membrane may be a proton exchange membrane.

Different compounds found in water electrooxidize at different anodic potentials. Some oxidize at relatively high potentials, higher than water itself. Choosing an electrode material with high overpotential for water oxidation opens the possibility of oxidizing those compounds with relatively high potentials.

Conductive boron-doped diamond is an example of a material with a high overpotential for oxygen evolution in aqueous solutions. Accordingly, this invention involves the use of boron doped-diamond ("BDD") electrodes for the electrochemical oxidation of the organics to $CO_2$. Such electrodes have been shown to possess attractive properties over conventional electrodes, like platinum. Properties of BDD electrodes include superior chemical and mechanical stability, stability against corrosion, low and stable voltammetric background currents, and a wide working potential window stemming from the high overpotentials for both oxygen and hydrogen evolution reactions. Thus, oxidation of a broad range of compounds in aqueous solution is possible. Electrochemical oxidation of organic compounds on doped diamond does not require harmful radiation or chemical oxidants as required in tradition UV-persulfate oxidation. In addition, BDD represents a safe, long lasting alternative to mercury vapor UV lamps which are environmentally hazardous and have a short service life.

Accordingly, in one embodiment, the oxidation module may have a pair of electrodes comprising a substrate material such as a rectangular silicon wafer coated with a doped-diamond film. The diamond dopant may be boron. The boron dopant serves to make the diamond electrically conductive. One of the boron-doped diamond (BDD) coated electrodes serves as an anode while the second BDD coated electrode serves as the cathode.

Accordingly, in one embodiment, the oxidation module may be a single-compartment cell where the analyte is directed through a single serpentine channel and allowed to contact the BDD anode and cathode in succession. An example of a suitable serpentine material is polychlorotrifluoroethylene (PCTFE). The serpentine provides electrical insulation between the two electrodes. The serpentine is constructed so as to maximize distance between the electrodes and maximize surface of the electrodes in contact with sample while keeping fluidic path volume to a minimum. With a single-compartment cell, there is no barrier separating the anode and cathode.

In another embodiment, the oxidation module may be a dual-compartment cell wherein a conductive membrane physically separates the anode and cathode. In the dual-compartment cell, the analyte is restricted to contact only the anode for oxidation. The dual-compartment cell may have a first compartment and a second compartment therein, with a conducting membrane separating the first and second compartments. The purpose of the conducting membrane is to physically separate the oxidized aqueous sample from the cathode while allowing protons from the oxidized aqueous sample to permeate the membrane thereby closing the electrical circuit. An example of a suitable conducting membrane is the proton exchange membrane made of a sulfonated tetrafluoroethylene based fluoropolymer, such as Nafion®, or membranes made of a similar material. The organics may be oxidized by applying a DC voltage between the anode and the cathode. Alternatively, the applied voltage may be in the form of a square wave.

This invention also relates to an electrochemical $CO_2$ sensor to detect and quantify the $CO_2$ generated from the electrooxidation step. The principle behind the detection relies on the use of a Pt electrode to measure $CO_2$ electrochemically based on redox reactions. Conventional TOC instruments based on membrane conductometric detection methods require the use of membranes that allow $CO_2$ to selectively pass through it. The detection scheme of the present invention enables the user to avoid the use of a membrane, conductivity cell, and a DI water loop. In addition, the reduction of $CO_2$ leads to the formation of a layer of chemisorbed $CO_2$, and the latter species is concentrated on the Pt electrode surface. This increases the sensitivity of the measurement process.

The $CO_2$ electrochemical measurement scheme of the invention relies on the principle that some metal catalysts, such as platinum, may reduce $CO_2$ and irreversibly adsorb the reduction product(s). First, $CO_2$ is concentrated on the surface of platinum-containing electrode as a chemisorbed layer by applying a cathodic potential. The chemisorbed layer is then oxidized to $CO_2$ by applying an anodic potential sweep. The electrical charge is measured and its magnitude correlated to the carbon concentration based on sample flow rate and the preconcentration step timing. Because the chemisorbed $CO_2$ oxidation signal occurs on the stripping curve in the same potential range where dissolved oxygen in sample is reduced, oxygen reduction is an interference. The oxygen reduction is proportional to the dissolved oxygen bulk concentration, while chemisorbed $CO_2$ reduction is proportional to the surface area of the electrode surface. Hence, rather than controlling the level of interfering oxygen, the $CO_2$ surface signal is enhanced by increasing the surface area of the Pt electrode through platinization. The surface area of the Pt electrode may also be increased by decorating it with gold adatoms.

Accordingly, in one embodiment, the carbon dioxide measurement module comprises an electrochemical cell containing working, reference, and auxiliary electrodes where the working electrode may be constructed of a material comprising platinum that reduces $CO_2$ and chemisorbs reduction products. Chemisorbed $CO_2$ is then oxidized back to $CO_2$ for quantification in an anodic stripping voltammetry sweep. Alternatively, the working electrode may be constructed of a material comprising platinized platinum. The working electrode may also be constructed of a mixture platinum (Pt) and gold (Au) or a platinum surface modified by decorating with gold adatoms. When the platinum surface is decorated with gold adatoms, individual gold atoms are adsorbed onto the platinum surface, increasing the roughness of the electrode, and thereby increasing the surface area.

In another embodiment, an apparatus for measuring total organic carbon in an aqueous stream is disclosed. The apparatus may comprise an oxidation module comprising at least one doped diamond electrode therein. The oxidation module may be configured to contact the aqueous stream with the doped diamond electrode and to apply an oxidizing potential to the doped diamond electrode thereby oxidizing any organics in the aqueous stream to form an oxidized aqueous stream. The apparatus may also comprise a carbon dioxide measurement module comprising at least one platinum electrode therein. The carbon dioxide measurement module may be configured to contact the oxidized aqueous stream with the platinum electrode and to apply a cathodic potential and thereafter apply an anodic potential to the platinum electrode. The apparatus may also comprise a fluid transfer module operatively connected to the oxidation module and the carbon dioxide measurement module and configured to transfer the oxidized aqueous stream from the oxidation module to the carbon dioxide measurement module. The apparatus may also comprise a control module operatively connected to the carbon dioxide measurement module and configured to measure an amperometric response of the platinum electrode and to equate the amperometric response of the platinum electrode to a total organic content of the aqueous stream. In yet another embodiment, the control module may be further operatively connected to the oxidation module and the fluid transfer module. In another embodiment of the apparatus, the platinum electrode may be platinized. Alternatively, the platinum electrode may be decorated with gold adatoms. In another embodiment, the doped diamond electrode may be a boron-doped diamond electrode. In another embodiment, the anodic potential may be an anodic potential sweep or an anodic potential step. The oxidizing potential may be a static anodic potential, an alternating potential waveform, or anodic potential pulses. In yet another embodiment, the oxidation module may further comprise a dual-compartment cell, wherein the dual-compartment cell has a first compartment with an anode therein and a second compartment with a cathode therein. In another embodiment, the dual-compartment cell may further comprise a conducting membrane that separates the first compartment from the second compartment. The conducting membrane may be a proton exchange membrane.

In another embodiment, a system for measuring carbon dioxide an aqueous stream is disclosed. The system may comprise a memory and a processor operatively connected to the memory. The processor may be configured to receive inputs, such as an amperometric response of a platinum electrode, and use the inputs to generate outputs, such as a total organic content of an aqueous stream. The processor may be further configured to store the outputs in the memory. The inputs comprising an amperometric response may be generated by contacting an aqueous stream with a platinum electrode, applying a cathodic potential to the platinum electrode and then applying an anodic potential to the platinum electrode while maintaining contact with the aqueous stream. In another system embodiment, the platinum electrode may be platinized. Alternatively, the platinum electrode may be decorated with gold adatoms. In yet another system embodiment, the inputs may further comprise a background amperometric response.

EXAMPLES

The examples are divided into two sets. Set 1 discloses various embodiments of the oxidation module. Set 2 discloses various embodiments of the $CO_2$ measurement module.

Example Set 1—Oxidation Module

Example 1.1—Boron-Doped Diamond Electrode

Example 1.1 demonstrates electrooxidation of organic compounds in water. Boron doped diamond (BDD) was used as the oxidizing electrode. A thin-film (app. 4 µm) of boron-doped diamond was vacuum-deposited on a polycrystalline silicon substrate (Adamant Technologies, Switzerland). The examples disclose multiple embodiments of oxidations cells suitable for use in the present invention.

Figure 2:
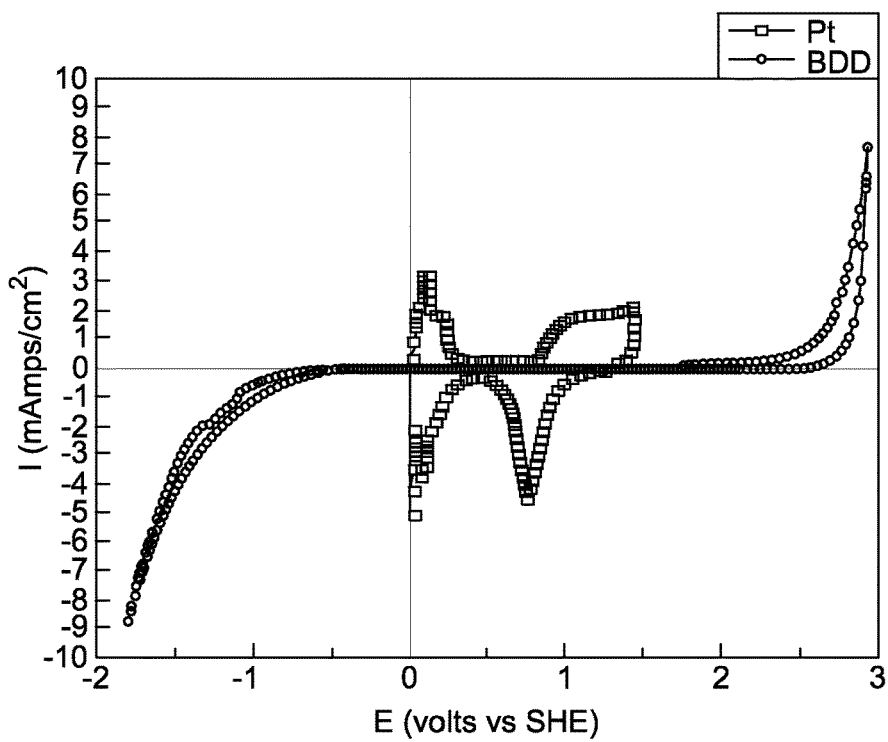
FIG. 2 shows the cyclic voltammetry of boron-doped diamond disk and platinum disk in 0.5M $H_2SO_4$.

For Example 1.1, bench-top experiments were performed with sulfuric acid as the electrolyte. The boron-doped diamond electrode comprised a doped-diamond film deposited on a polycrystalline silicon disk (3.7 mm) FIG. 2 shows the cyclic voltammetry of a BBD disk as compared to a platinum disk, both in 0.5M $H_2SO_4$. With the nearly flat double layer region and a very wide accessible potential window of water stability, the BDD shows its suitability for oxidation of organic compounds.

Example 1.2—Oxidation of Organic Compounds

The BDD electrode above was then used to oxidize various organic compounds. The same experimental setup as in Example 1.1 was used. Methanol, isopropanol and sucrose were chosen as the organic compounds for the experiments (all Aldrich).

Figure 3:
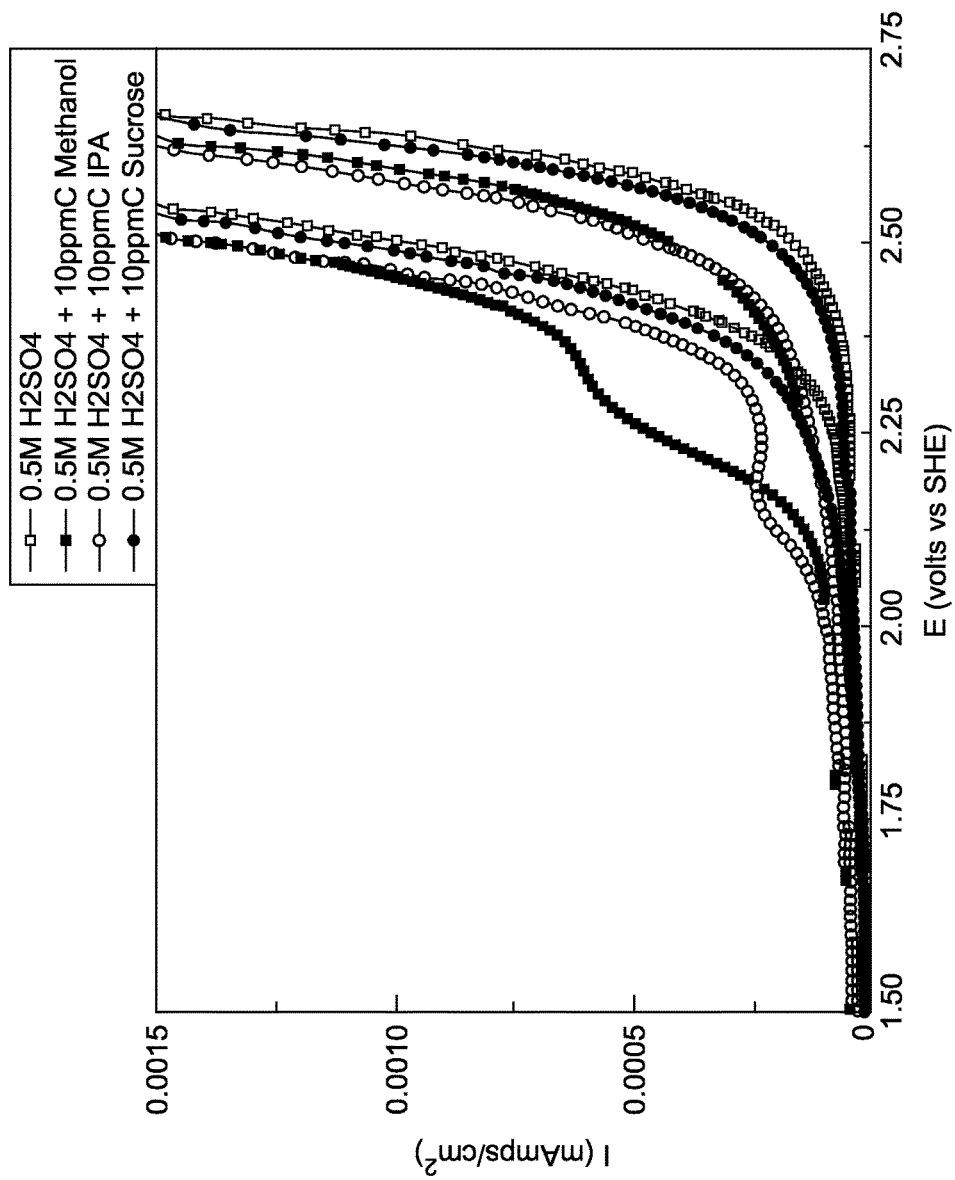
FIG. 3 shows the voltammetry of boron-doped diamond in acidic solutions of various organic compounds.

Organics oxidation manifests itself on the anodic part of cyclic voltammograms. As shown on FIG. 3, the different organic compounds generate different voltammograms.

Methanol, isopropanol and sucrose showed oxidation in less anodic potentials than water oxidation. Without limiting this disclosure to one theory of operation, it is believed that the organics were directly oxidized on the electrode without water intermediates, i.e. OH radicals, leading to the resolution in the oxidation potential between the different compounds.

Figure 4:
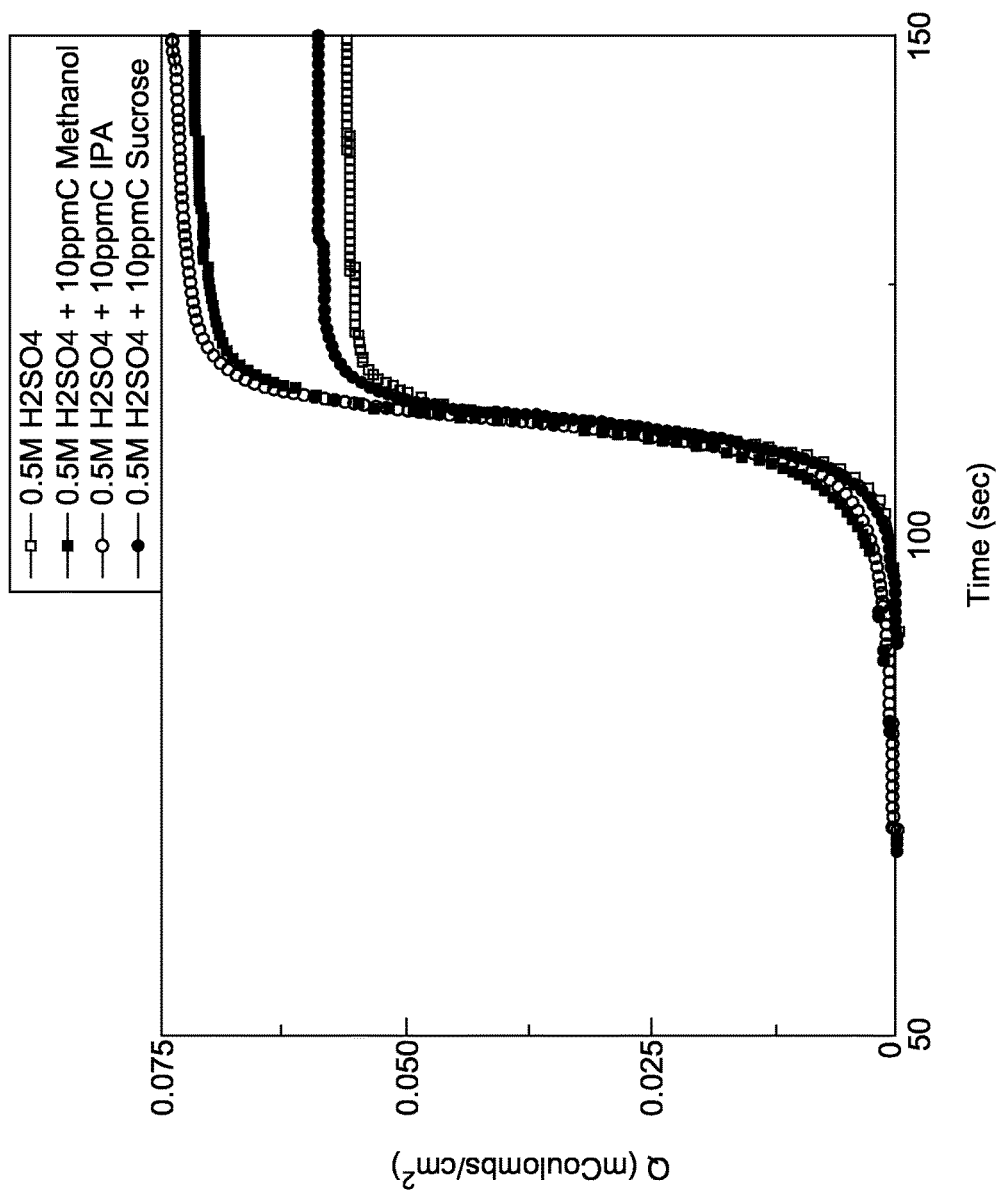
FIG. 4 shows the coulometry of boron-doped diamond in acidic solutions of various organic compounds.
Figure 5:
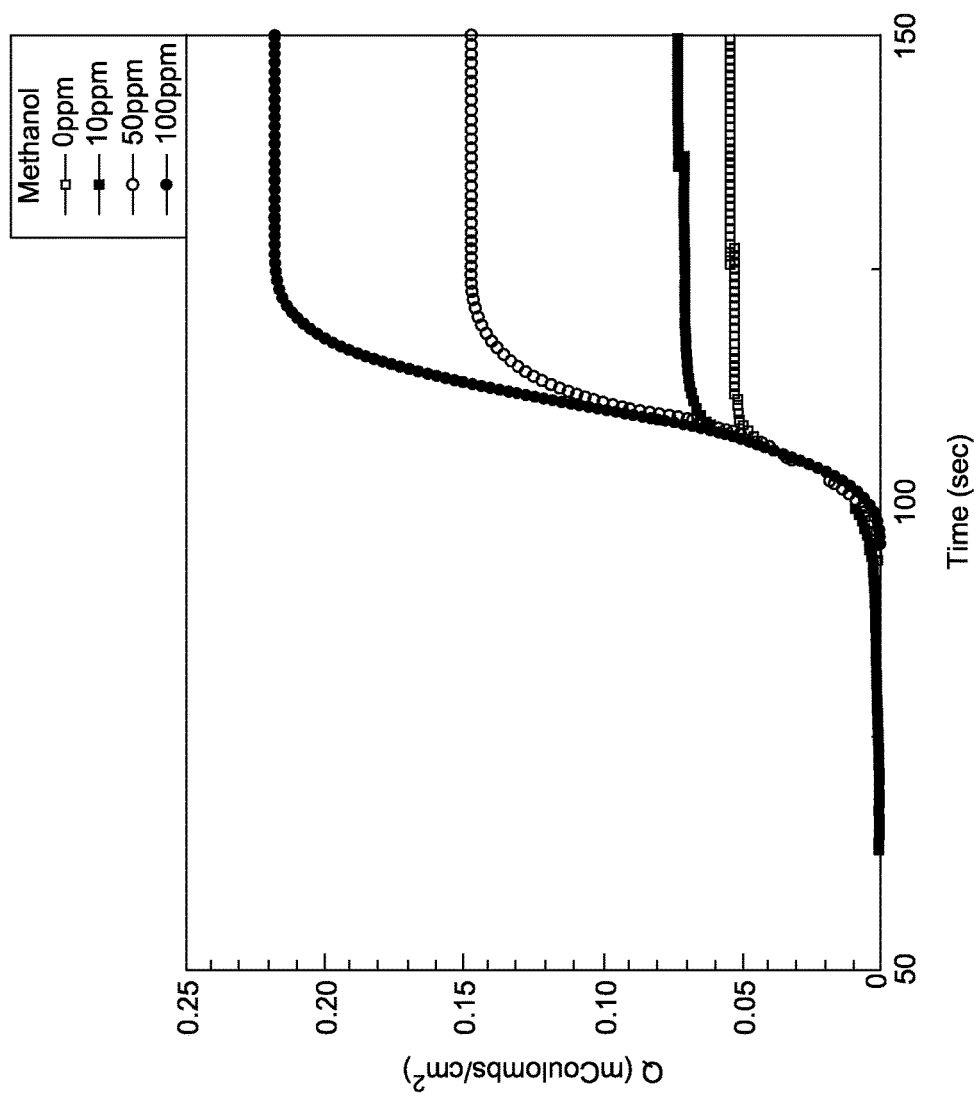
FIG. 5 shows the coulometry of boron-doped diamond in 0.5M $H_2SO_4$ with varying concentrations of $CH_3OH$.

Coulometry results are presented in FIGS. 4-5. FIG. 4 shows the coulometry of boron-doped diamond in aqueous solutions of various organic compounds. The two alcohols have a higher recovery than sucrose. However, this may be only an apparent difference as a result of one or more factors. One factor may be sucrose's different number of electrons needed to oxidize one carbon atom (electron to carbon ratio). The concentrations of the organics tested were based on carbon content. Therefore sucrose required less of a charge to transform into carbon dioxide than the alcohols. The electron to carbon ratios of the tested organic compounds are shown in the following equations.

Methanol:

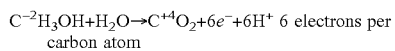
$C^{-2}H_3OH+H_2O \rightarrow C^{+4}O_2+6e^-+6H^+$ 6 electrons per carbon atom Propanol:

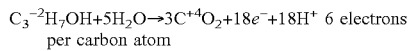
$C_3^{-2}H_7OH+5H_2O \rightarrow 3C^{+4}O_2+18e^-+18H^+$ 6 electrons per carbon atom Sucrose:

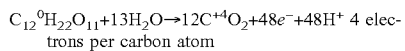
$C_{12}^{0}H_{22}O_{11}+13H_2O \rightarrow 12C^{+4}O_2+48e^-+48H^+$ 4 electrons per carbon atom The relationship between the oxidation charge and the concentration was verified using methanol. FIG. 5 shows the coulometry of BDD in 0.5M $H_2SO_4$ with varying concentration of methanol ($CH_3OH$). As can be seen in FIG. 5, increased methanol concentration requires an increased charge for oxidation. There was no saturation or starvation observed even with 100 ppm C methanol.

Example 1.3—Prototypes of the Oxidation Module

Example 1.3 A—A Single-Compartment Cell

Figure 6:
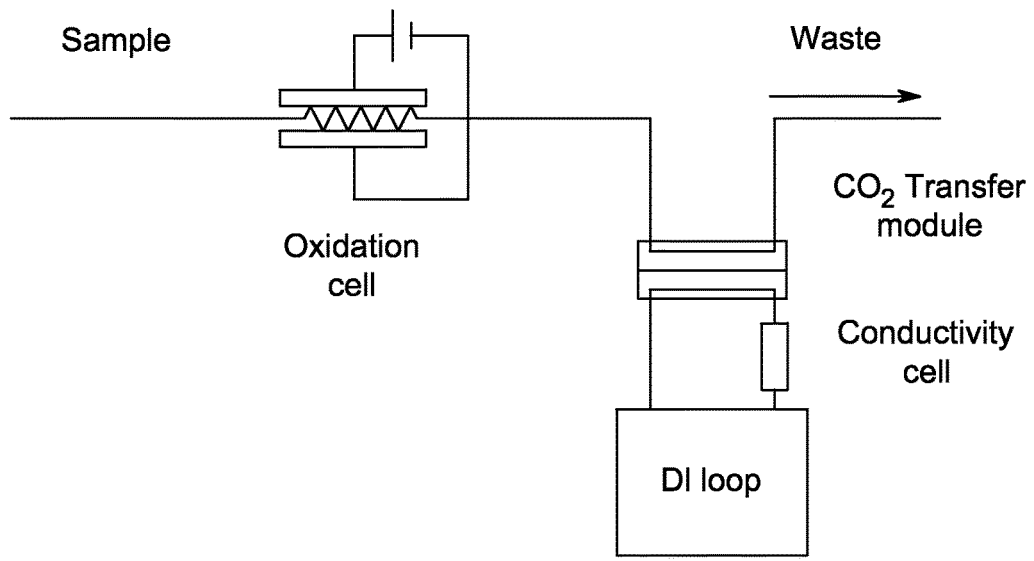
FIG. 6 shows an embodiment of a TOC analyzer.

A bench-top TOC analyzer was built. It had the configuration shown in FIG. 6. The $CO_2$ concentration, and thus efficiency of the oxidation cell, was measured via membrane conductivity using a Sievers 900 TOC Analyzer (GE Analytical Instruments).

Figure 7:
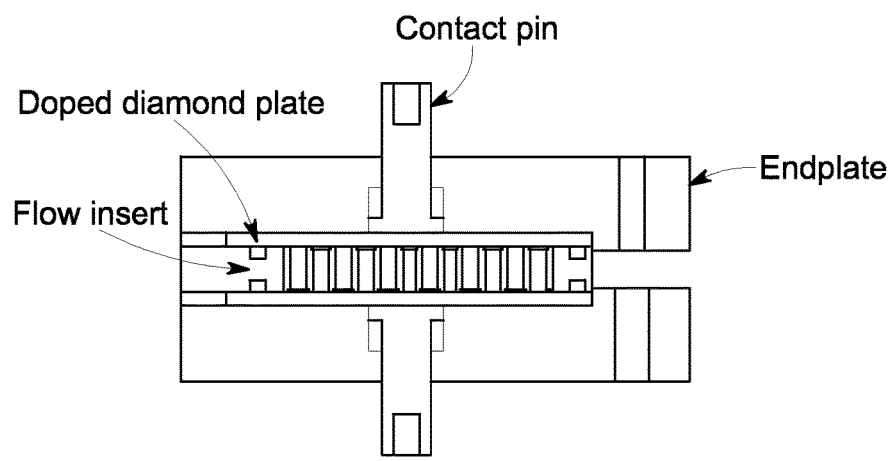
FIG. 7 shows a cross section of an embodiment of an oxidation module comprising a single-compartment cell.
Figure 8:
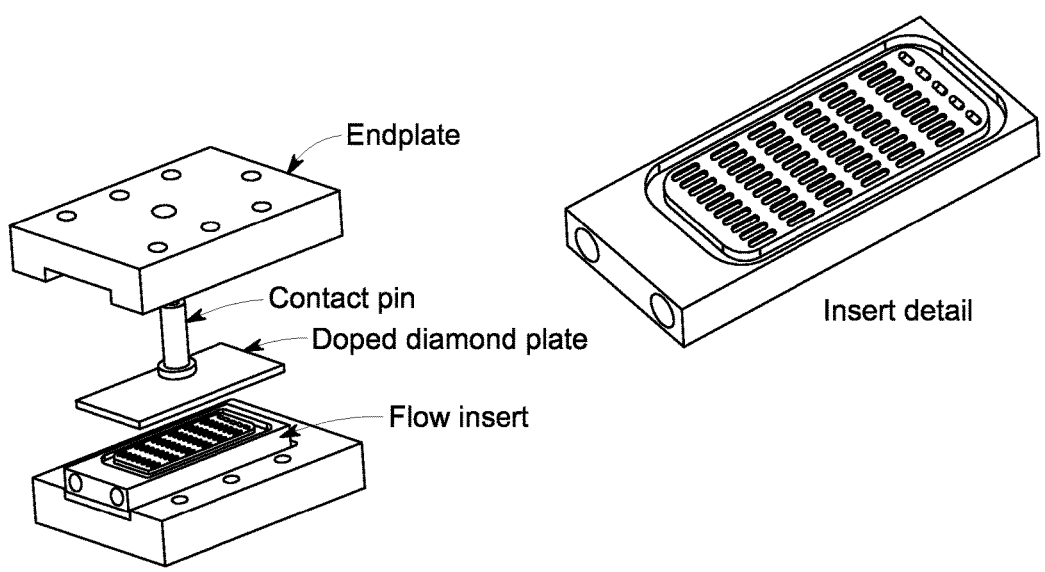
FIG. 8 shows an exploded view of an embodiment of an oxidation module comprising a single-compartment cell.

For Example 1.3 A, the sample was directed through a single-compartment cell comprising a single serpentine channel and allowed to contact two electrodes in succession. FIG. 7 is a cross section of a single-compartment cell with a flow insert and a rectangular doped diamond electrode-plate. FIG. 8 shows an exploded view of an embodiment of a single-compartment cell.

As seen in FIG. 7-8, the electrodes were rectangular polycrystalline silicon wafers (2.5×5 cm) coated with boron-doped diamond deposits (Adamant Technologies, Switzerland). The serpentine channel, also referred to as an "insert" or "flow insert", made from polychlorotrifluoroethylene (PCTFE) (Neoflon, Daikin Industries) provided electrical insulation between the two electrodes. The single-compartment cell was constructed in a way to maximize the distance between the electrodes and maximize the surface of the electrodes in contact with sample while minimizing the fluid path volume. The achieved fluid path volume was 0.525 ml and the electrode surface area exposed to sample was 1.886 $cm^2$ per electrode.

Figure 9:
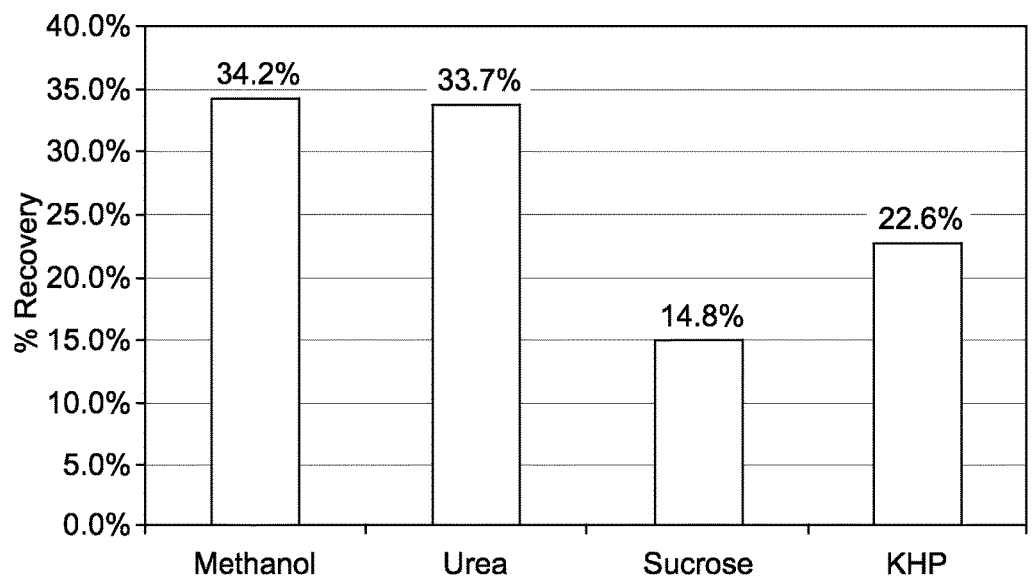
FIG. 9 shows the recovery of 3 ppm C of aqueous solutions of various organic compounds at a flow rate of 50 μl/min.

Aqueous solutions of methanol, potassium hydrogen phthalate (KHP), sucrose and urea (all Aldrich, ACS reagents) were oxidized using the single-compartment oxidation cell. The concentration of all the solutions was 3 ppm C. The electrolyte was 0.5 M $H_2SO_4$. A DC voltage of 5.5 V was chosen as generating the highest oxidation efficiencies. The sample flow rate was 50 µl/min with a corresponding residence time of 10.5 minutes. The TOC recoveries of various aqueous solutions are shown in FIG. 9. The % TOC recovery was approximately 34% for methanol and urea, 23% for KHP, and 15% for sucrose.

Figure 10:
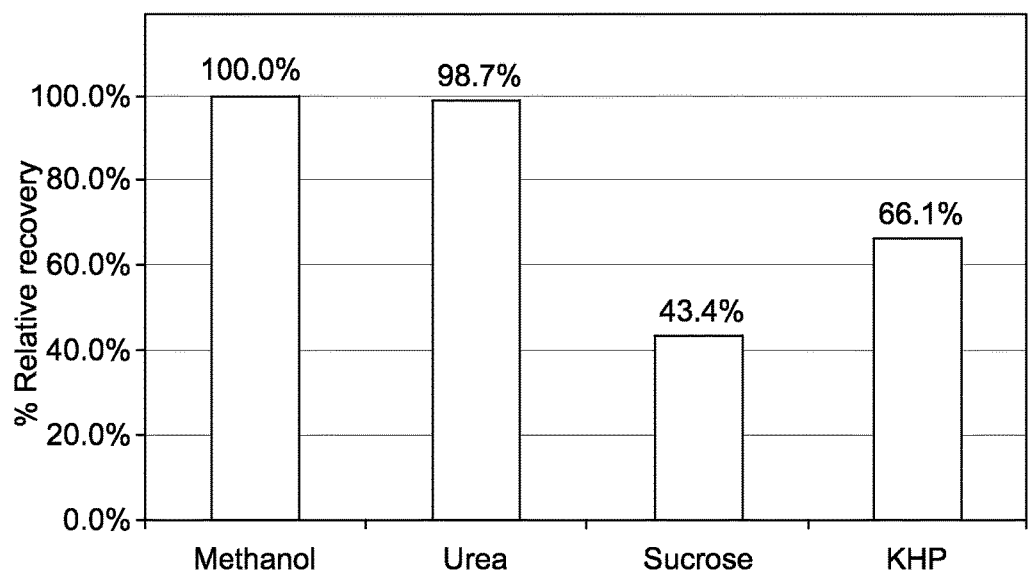
FIG. 10 shows the relative recovery of 3 ppm C of selected compounds normalized to the recovery of 3 ppm C of methanol.

Methanol recovery was used as a benchmark for Example 1.3 A. FIG. 10 shows the relative % TOC recovery of the tested compounds normalized to methanol.

As can be seen in FIGS. 9-10, the recoveries of sucrose and KHP are low, with sucrose's TOC recovery under 50% of that of methanol. Without limiting this disclosure to one theory of operation, the low recoveries may be the result of formation of intermediates during oxidation that form redox couples. These couples may undergo repeated oxidation-reduction when passing over anode and cathode. As a result, oxidation may not be complete and the intermediates may exit the oxidation module producing the observed lower TOC recoveries.

In electrolysis, as a direct consequence of Maxwell's equations, when current flows through an electrolyte, one electrode (anode) supports oxidation while the opposite electrode (cathode) supports reduction. Therefore, in a single-compartment cell, the sample undergoes oxidation as well as reduction as it flows through the cell. If the particular sample contains a reversible redox system, it will proceed towards equilibrium rather than total oxidation.

Example 1.3 B—Dual-Compartment Cell

Figure 11:
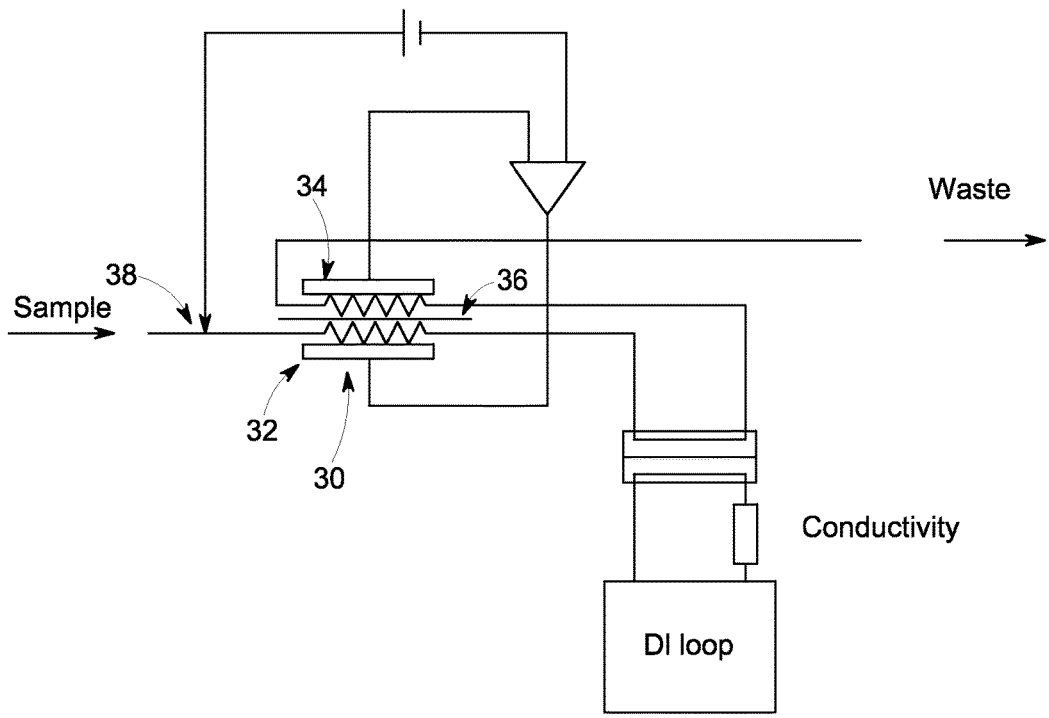
FIG. 11 shows an embodiment of a TOC analyzer with oxidation module with separated oxidation and reduction compartments.

Accordingly, in Example 1.3 B, a dual-compartment cell that separated oxidation from reduction was tested. The schematic of the prototype TOC analyzer with a dual-compartment cell is shown in FIG. 11. The dual-compartment cell (30) comprised an anode (32) and cathode (34), one flow channel wherein the sample contacts only the anode, and one flow channel wherein the sample contacts only the cathode. A proton exchange membrane (36) separated the two channels while maintaining continuity of the electrical circuit (Nafion® N117, Ion Power). The Ag/AgCl reference electrode (38) was placed outside the oxidation cell and contacted the sample before the anode (32).

Figure 12:
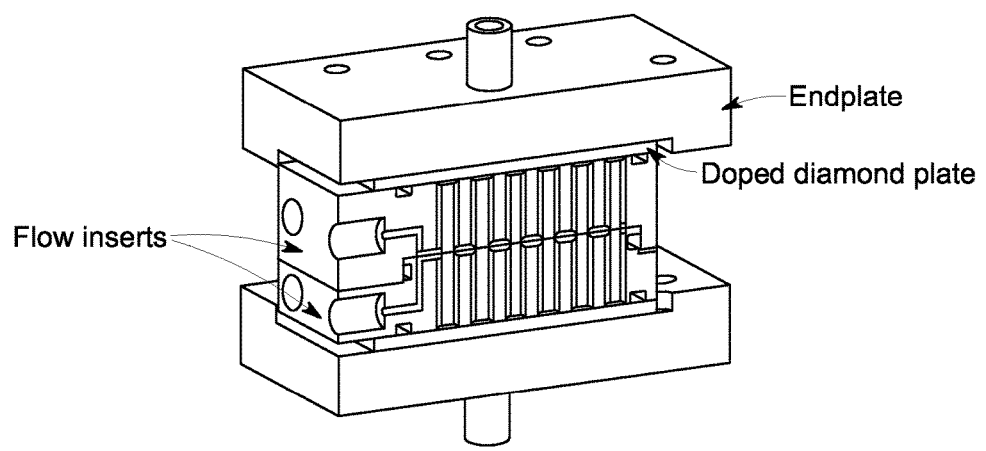
FIG. 12 shows a cross section of an embodiment of an oxidation module comprising a dual-compartment cell.
Figure 13:
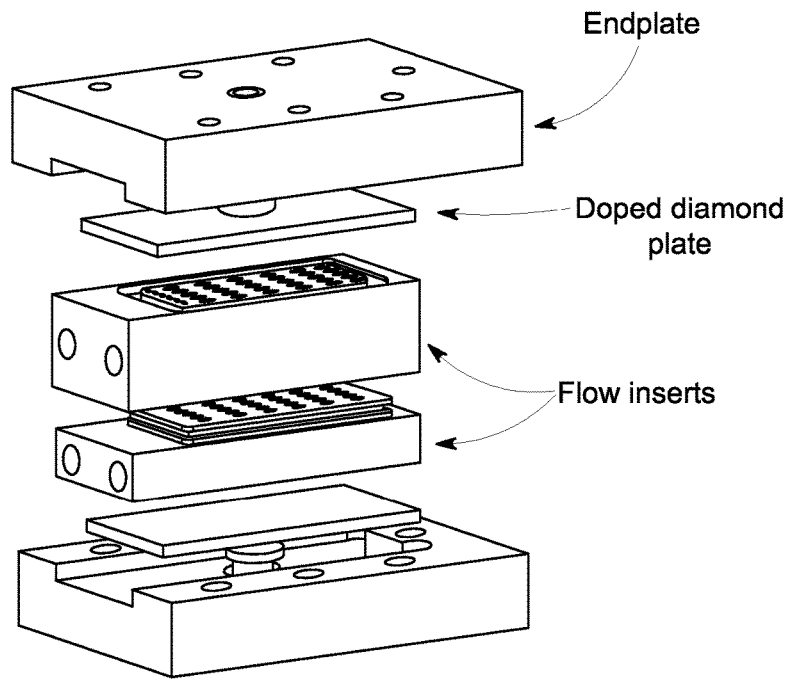
FIG. 13 shows an exploded view of an embodiment of an oxidation module comprising a dual-compartment cell.

The dual-compartment cell is an expansion of the single-compartment cell in Example 1.3 A. A cross section of the dual-compartment cell with two flow inserts is shown in FIG. 12. FIG. 13 shows an exploded view of the dual-compartment cell. A Nafion® membrane (not shown) was placed between the two flow inserts to separate the anode from the cathode. The electrode surface area exposed to the sample did not change (1.886 $cm^2$). However, the fluid path volume nearly doubled to 0.942 ml per side. The channel depth adjacent to the Nafion® membrane increased in size for the double-partition cell to maintain sample flow. The enlargement was dictated by the Nafion® membrane's tendency to expand when exposed to water or other solvents. As the membrane expands, it may restrict sample flow in the channels adjacent to it.

For Example 1.3 B, the applied voltage was controlled by a potentiostat (Solartron 1280B). Aqueous solutions of methanol, potassium hydrogen phthalate, sucrose and urea (all Aldrich) were oxidized using the dual-compartment cell. The concentrations of all the solutions were 3 ppm C. The electrolyte was 0.5 M $H_2SO_4$.

Figure 14:
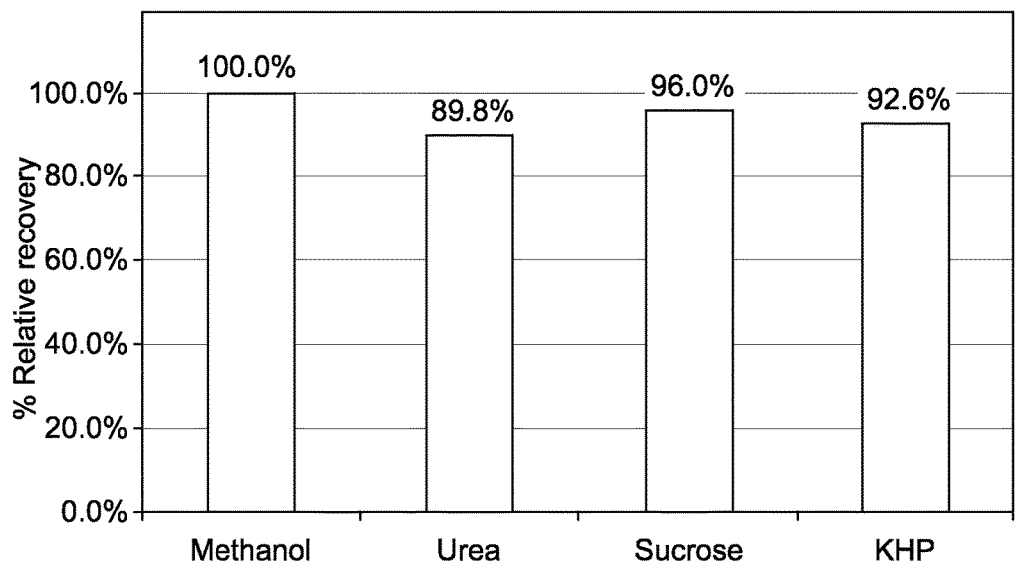
FIG. 14 shows the relative recovery of 3 ppm C of selected compounds in a Nafion®-separated dual-compartment cell.

The introduction of a membrane separator into the dual-compartment cell limited sample contact to only the anode. As can be seen in FIG. 14, the recovery of sucrose and KHP improved. These results confirmed the intermediates hypothesis.

Figure 15:
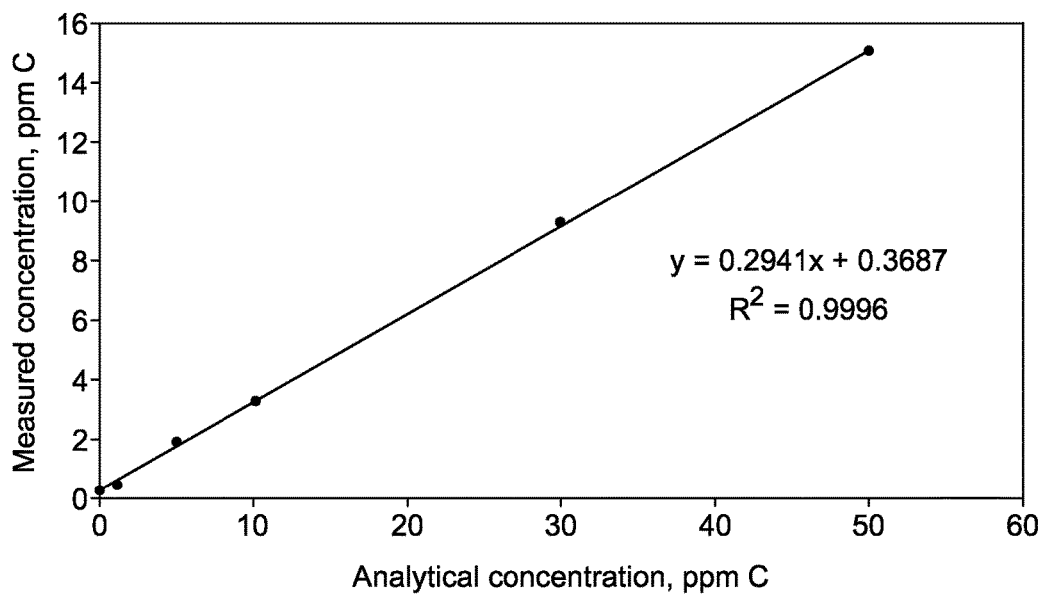
FIG. 15 shows the sucrose concentration recovery in a Nafion®-separated oxidation cell.

The dual-compartment cell performance was also tested for higher TOC concentrations. The response for sucrose is shown in FIG. 15. In the range tested, (3-50 ppm C) there is almost a perfect linear response.

Example Set 2—$CO_2$ Measurement

The examples in Example Set 2 demonstrate how dissolved organic carbon is measured by electrochemical methods. More specifically, the examples show how carbon present in the analyte may form a self-assembled layer (submonolayer) of chemisorbed carbon monoxide on the surface of an anode in the preconcentration step followed by stoichiometric oxidation to carbon dioxide in the anodic stripping step.

Example 2.1—System Suitability Test

Figure 16:
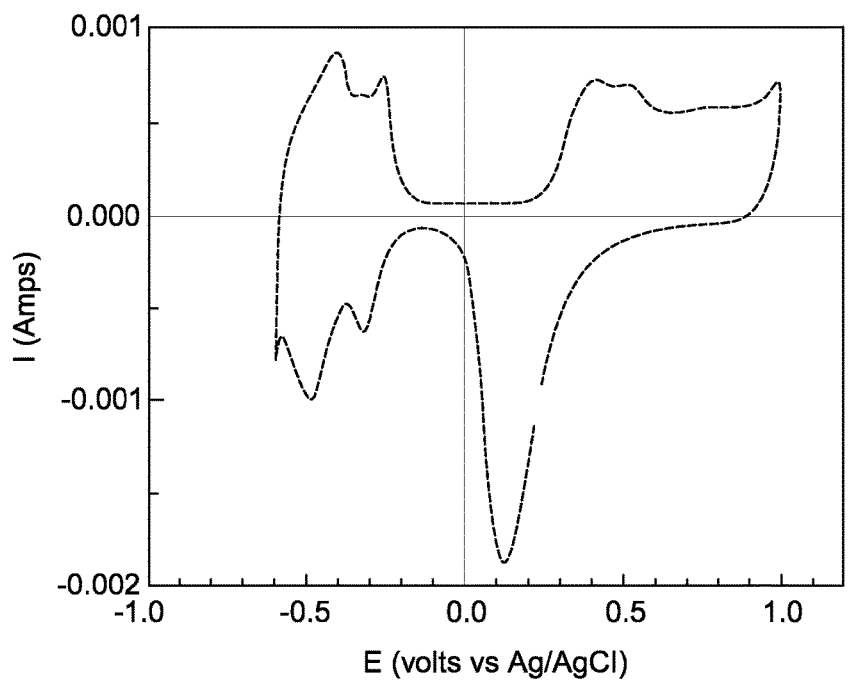
FIG. 16 shows the cyclic voltammetry of platinum in 0.5M $H_2SO_4$ recorded in a conventional electrochemical environment.

For Example 2.1, experiments were performed in a conventional electrochemical cell. A 3-mm platinized platinum disk fitted in a PEEK housing served as working electrode. Platinized platinum gauze, 1 in.×1 in., was used as an auxiliary electrode. A cross-section of a 0.5-mm diameter silver wire covered with silver chloride was the reference electrode. Both working and reference electrodes were part of a flow cell (BAS). A solution of 0.5 M $H_2SO_4$ made a supporting electrolyte. The cell was controlled by a potentiostat (Solartron 1280B). The system suitability was checked by cyclic voltammetry shown in FIG. 16. The potential sweep rate was 100 mV/sec.

The shape of current-potential curve was excellent. Some distortions were minimal and largely due to high roughness of the electrode. Real surface of the electrode calculated from the data presented in FIG. 16 was 13.5 $cm^2$. Hence, the roughness factor of the electrode was almost 200 (geometric area of the electrode disk was 0.07 $cm^2$). There was no indication of any $CO_2$ present in the solution. This curve represented system background response.

Figure 17:
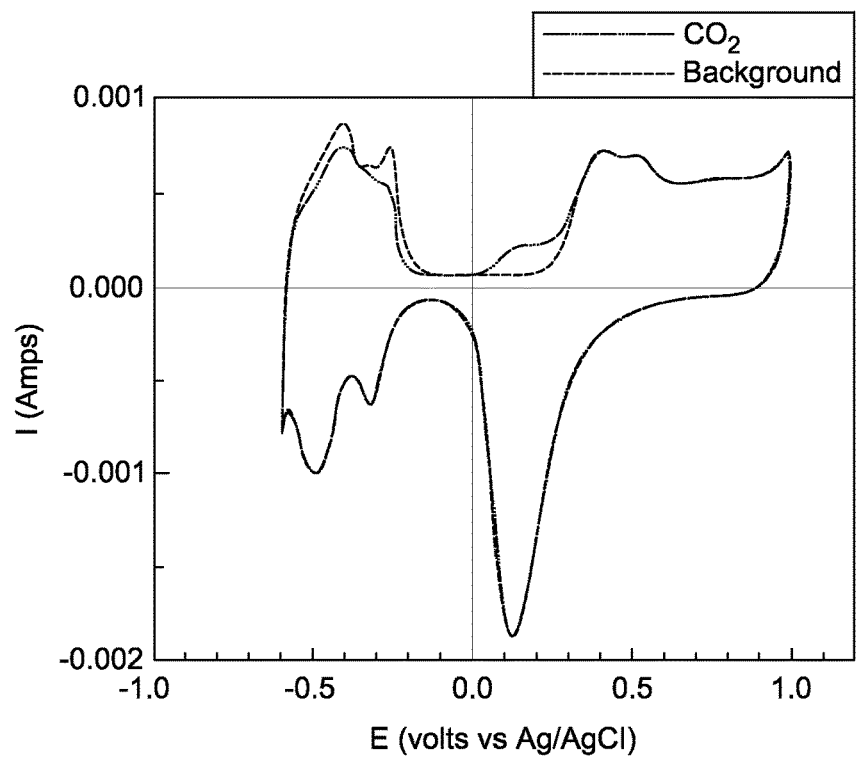
FIG. 17 shows the cyclic voltammetry of platinum in 0.5M $H_2SO_4$ with and without $CO_2$ present (background response).

The next step was to saturate solution with gaseous $CO_2$. The voltammetric response in these conditions, together with background curve (no $CO_2$ present), is presented in FIG. 17. The $CO_2$ influenced cyclic voltammetry in two regions: 1) a decrease in the hydrogen ionization cluster peaks in the cathodic part of the curve, and 2) an appearance of additional oxidation peak in the anodic part of the curve.

The cyclic voltammetry of the test system changes for the following reasons. Carbon dioxide present in the solution cannot be further oxidized and remains inactive during anodic polarization of the platinum. However, carbon dioxide is reduced on cathodic polarized platinum to form "reduced chemisorbed species". Formation of these species proceeds through displacement of hydrogen chemisorbed on the electrode. The current associated with the reduction is small because the process is diffusion limited and cannot be directly recorded during voltammetry experiments. But, a decrease in hydrogen surface coverage is recorded in the form of decreased hydrogen ionization peaks. The chemisorbed species derived from carbon dioxide remains on the surface until the potential threshold for adsorbed water oxidation on platinum is reached. Oxidation of the chemisorbed species occurs just before the platinum is oxidized.

Following these experiments, there are two significant observations to make. First, the $CO_2$-specific analytical signal to be used is the oxidation peak of the chemisorbed $CO_2$-derived species. The reduction in hydrogen coverage is not $CO_2$ specific because many potentially interfering compounds present in sample water may displace adsorbed hydrogen as well. Second, the chemisorption of $CO_2$ during cyclic voltammetry is inadequate to produce a significant analytical signal for lower $CO_2$ concentrations.

Example 2.2—$CO_2$ Detection Scheme

Figure 18:
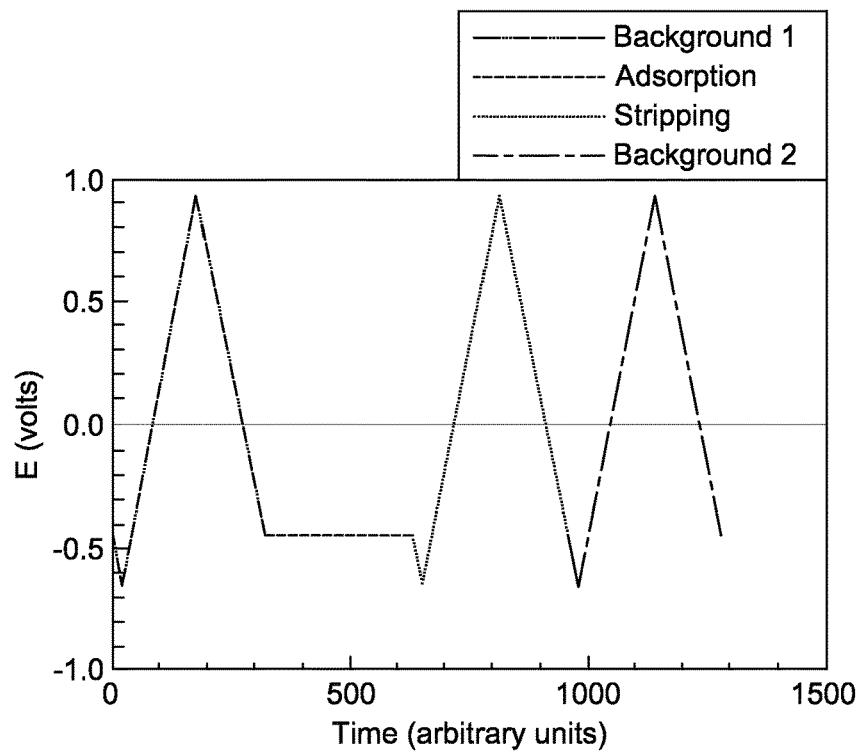
FIG. 18 shows an embodiment of a potential-time program applied to platinum in a $CO_2$ detection module.

The above mentioned properties of the analytical system led to the development of a $CO_2$ detection scheme. The potential-time program is shown in FIG. 18. The potentiostatic adsorption step ("Adsorption"), the cyclic voltammetry step ("Stripping") and the background scans ("Background 1" and "Background 2") are shown in the potential-time program. Cyclic voltammetry is used in the full potential range instead of a classic anodic-only voltammetric stripping sweep in order to ensure reproducibility of the electrode conditions for both analytical and background sweeps.

Figure 19:
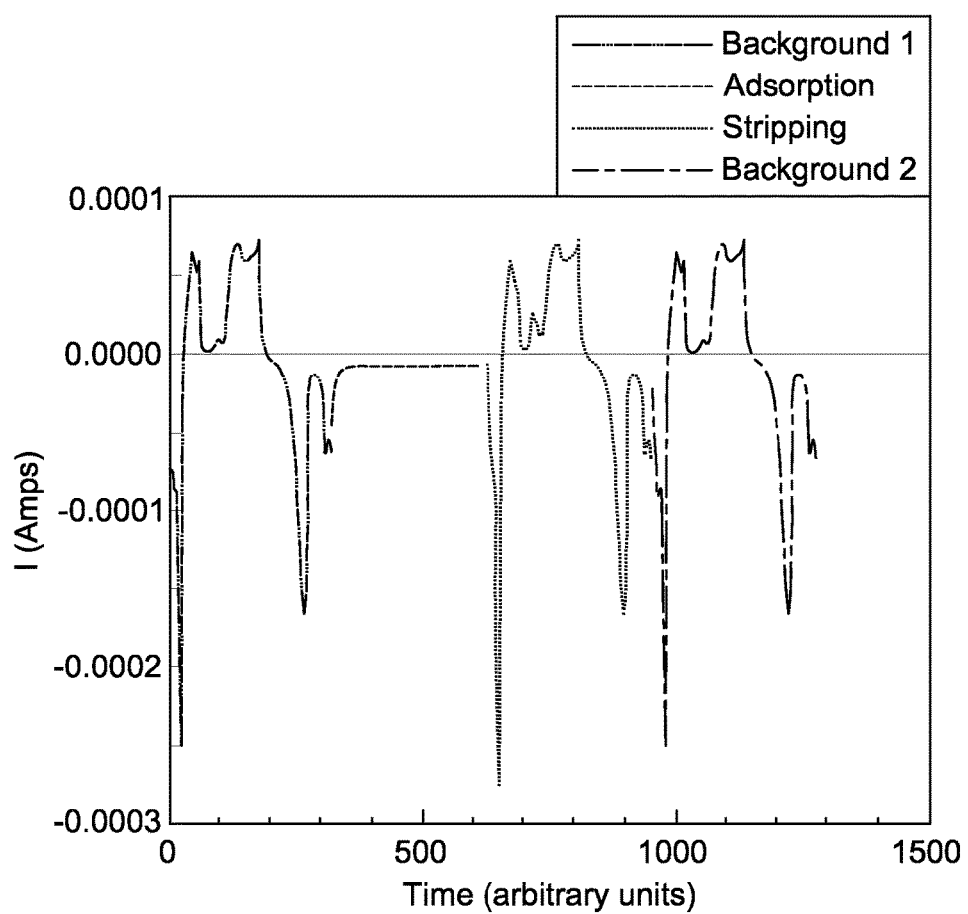
FIG. 19 shows the current response to the potential-time program presented in FIG. 18.

The $CO_2$ detection scheme includes an initial cyclic voltammetric sweep provided for monitoring the correctness of the whole system prior to each experiment. This step is not used for analytical purposes. The current needed to execute a potential-time program is shown in FIG. 19. An oxidation peak that serves as an analytical signal can be easily identified on the anodic voltammetric stripping portion of the cycle ("Stripping") in comparison to the background scans ("Background 1" and "Background 2"). As expected, both the Background 1 and Background 2 background scans are almost identical.

Although not included in the examples, an alternative potential-time program exits. It is possible to execute a potential double-anodic step instead of a stripping voltammetric potential sweep.

Example 2.3—"Flow-Through" $CO_2$ Measurement

Several factors may affect $CO_2$ measurement using flow-through testing equipment. These factors must be understood before the $CO_2$ measurements are made so testing parameters may be developed to compensate for the effects. The experiments in Example 2.3 are aimed at understanding the $CO_2$ measurement system's background response and developing the appropriate measurement parameters for flow-through testing.

Figure 20:
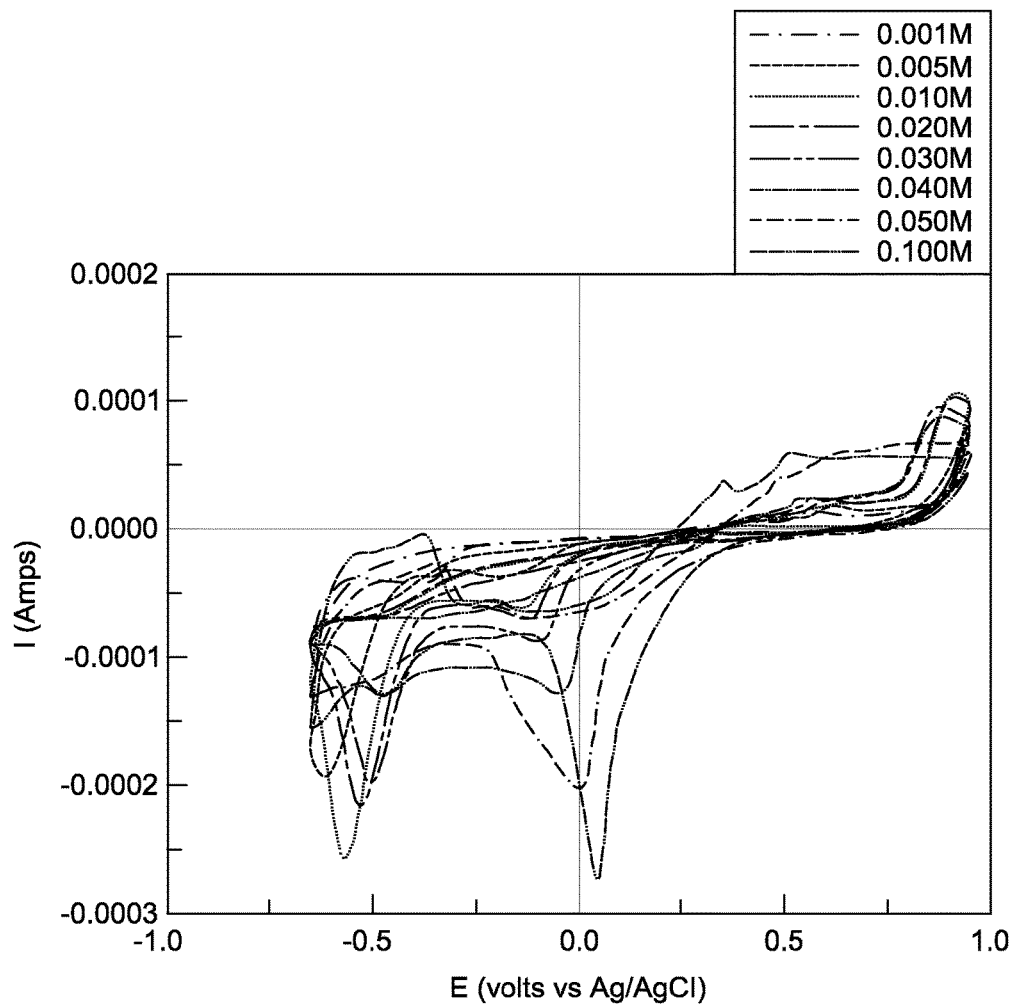
FIG. 20 shows the cyclic voltammetry of a "flow-through" embodiment of the $CO_2$ detection module.

The system dependency on concentration of the supporting electrolyte ($H_2SO_4$) is shown in FIG. 20. An acidified sample was directed through the flow-through sensor by using a syringe. The potential sweep rate was 10 mV/sec. The sample flow rate was 100 µl/min. The voltammogram at an acid concentration of 0.1 M has all the features of platinum voltammetric behavior; therefore the $H_2SO_4$ at a concentration of at least 0.1 M was accepted for further experiments.

Figure 21:
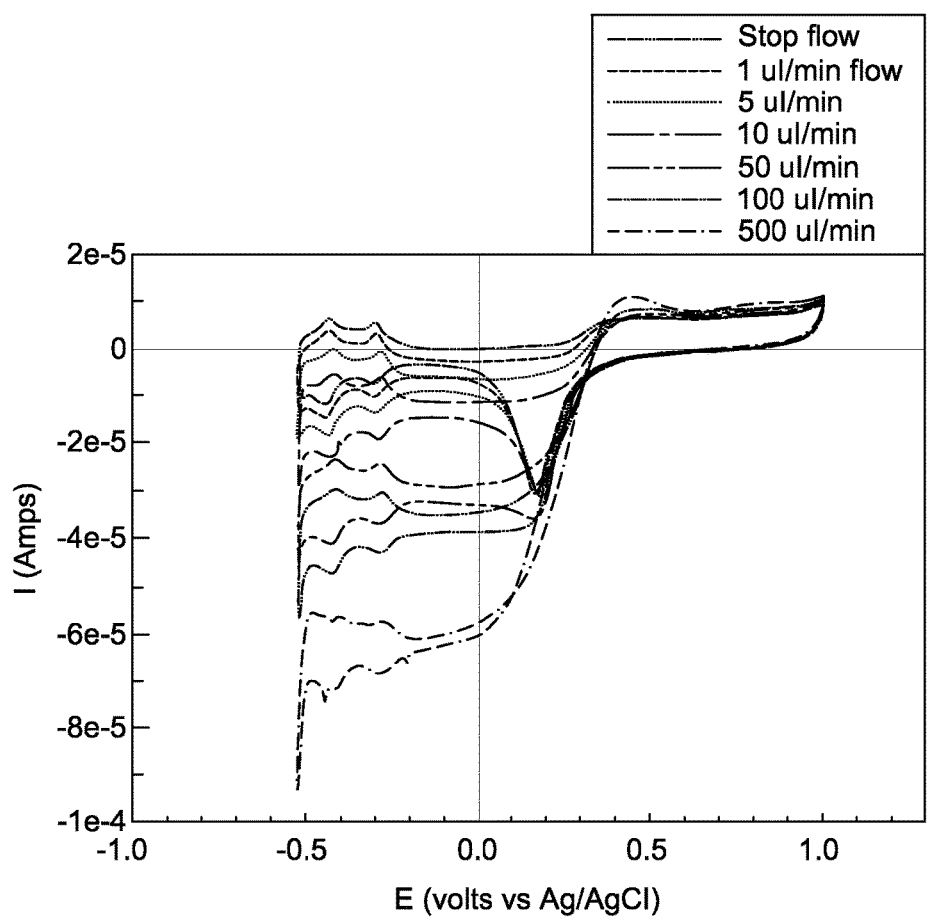
FIG. 21 shows the cyclic voltammetry of a flow-through system in 0.1M of $H_2SO_4$ at different flow rates.

Sample flow rate is a factor that affects $CO_2$ measurement. Oxygen dissolved in a sample (for samples exposed to air) reduces on platinum. The corresponding reduction current is proportional to the apparent concentration of oxygen on the surface of the electrode. In stationary conditions (no electrolyte replenishment or mixing), a diffusion layer develops, bringing the oxygen surface concentration down to zero and minimizing reduction current. Stationary conditions are often referred to as "stop flow" conditions in this disclosure. This stop flow situation is illustrated in FIG. 21. FIG. 21 shows the cyclic voltammetry of an flow-through system in 0.1M of $H_2SO_4$. The potential sweep rate was 40 mV/sec. Sample flow rates are indicated on the graph.

As soon as the diffusion layer is disturbed by the flowing sample, the electrolyte in the vicinity of the electrode is replaced and a quasi-stationary oxygen reduction current develops. The magnitude of this current depends on the flow rate. This phenomenon for different acid sample flow rates is also illustrated in FIG. 21.

Because the current from the oxidation of chemisorbed $CO_2$ occurs on the voltammetric curve in the same potential range as the oxygen reduction, the oxygen reduction is considered an interference. In addition, control of the oxygen content of the analyte is rather difficult. Therefore, instead of controlling the level of oxygen and other possibly interfering agents, the $CO_2$ signal may be amplified leaving the oxygen reduction signal unchanged.

Anodic stripping voltammetry with preconcentration takes advantage of producing surface species for oxidation. This makes the analytical signal independent from the electrolyte bulk concentration and diffusion of any interfering species. Anodic stripping voltammetry is dependent on the surface coverage of adsorbed species, which, in the case of $CO_2$ surface species, are irreversibly chemisorbed on platinum. A well-known process of platinizing the platinum results in an enlargement of the electrode real surface area by increasing the electrode roughness. Surface currents are increased by orders of magnitude leaving the bulk solution currents unaffected. This results in an oxygen reduction process that is below the detection limit.

Figure 22:
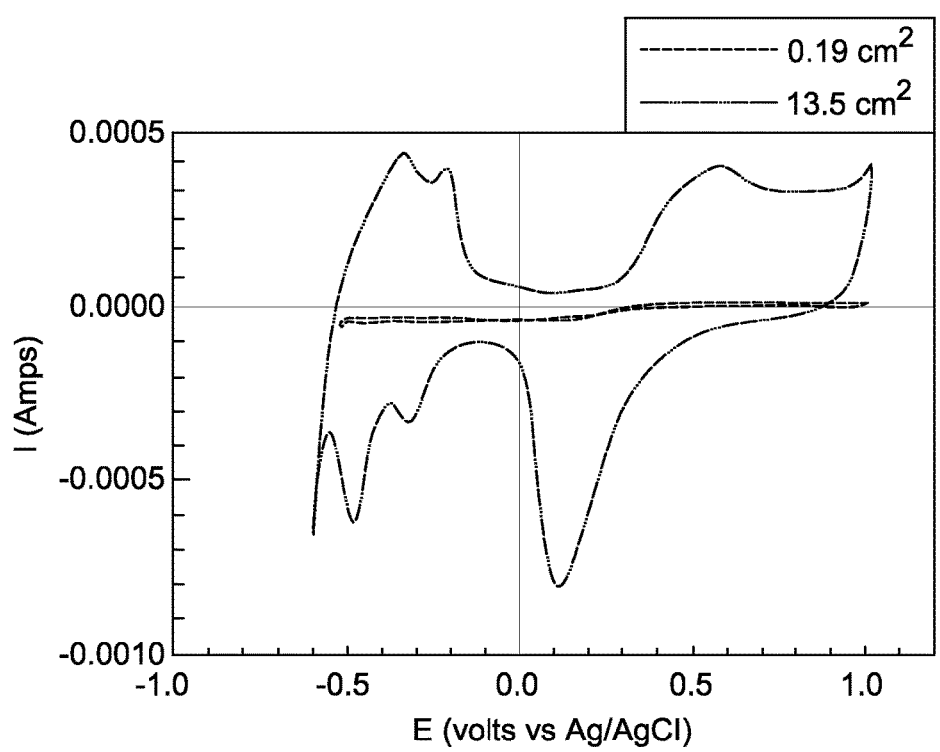
FIG. 22 shows the cyclic voltammetry comparison of a smooth platinum electrode and a platinized platinum electrode in a conventional electrochemical environment.

Voltammetry of a flow-through sensor after platinization in 0.1 M $H_2SO_4$ is shown in FIG. 22. The sample flow rate was 100 μl/min and the potential sweep rate was 40 mV/sec. For comparison, a voltammogram for the same electrode before platinization is also shown. The surface area of the original electrode was 0.19 $cm^2$ and after platinization 13.5 $cm^2$ (geometric area was 0.07 $cm^2$). Therefore, the electrode surface area was increased approximately 70 times. In other words, the surface concentration of $CO_2$ derived species was increased so the species could be detected while the oxygen related current remained at the background level.

Figure 23:
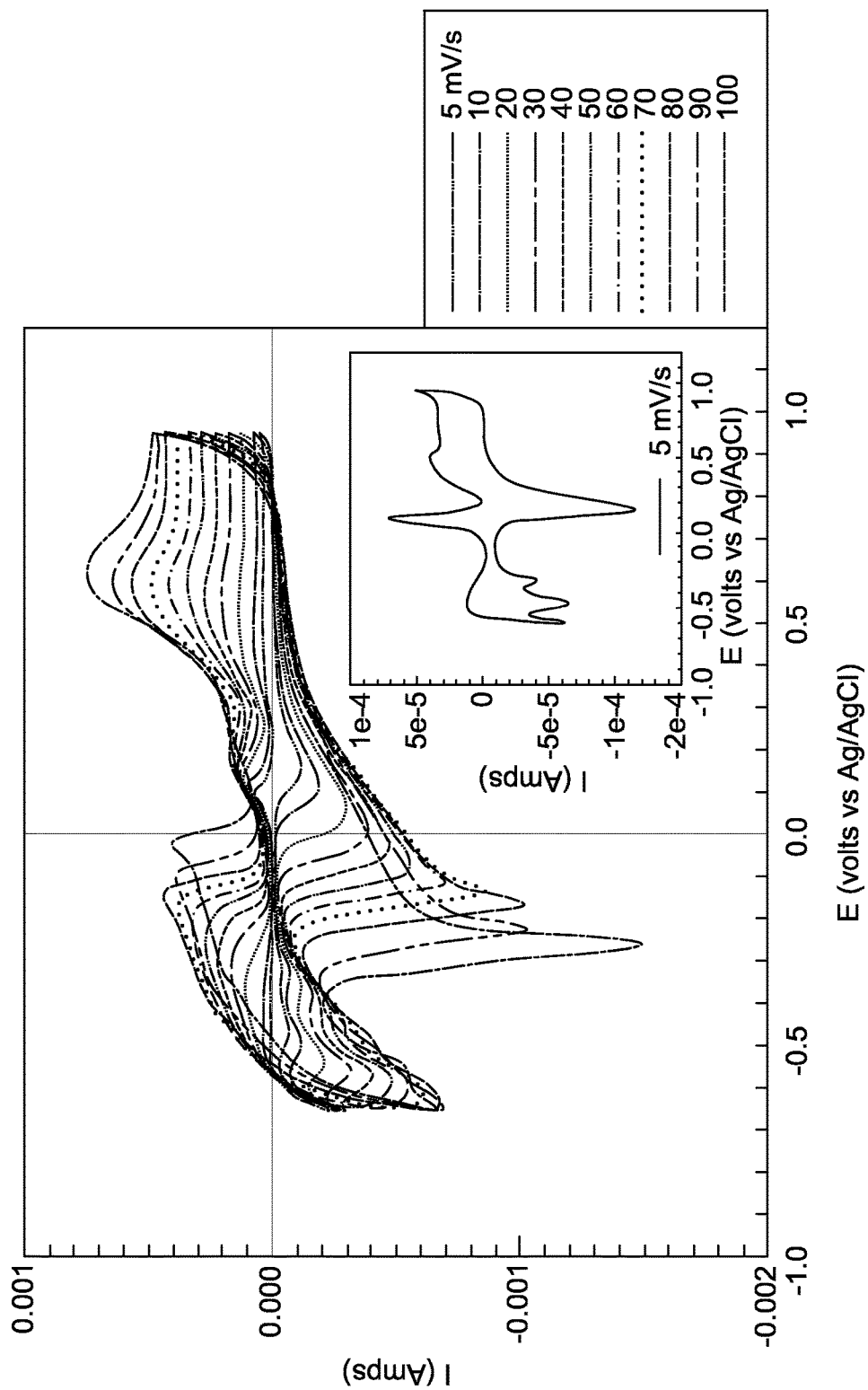
FIG. 23 shows the cyclic voltammetry of a flow-through embodiment of a $CO_2$ sensor in 0.1M $H_2SO_4$ at different potential sweep rates.

Voltammetric current is also dependent on potential sweep rate. FIG. 23 presents cyclic voltammetry for the $CO_2$ sensor recorded flow-through with varying potential sweep rates. The solution was 0.1 M $H_2SO_4$ with a flow rate of 100 μl/min. As can be seen in FIG. 23, the current features of platinum are shifted with applied potential sweep rate. As a result, the $CO_2$ related current, clearly visible during a slow scan (FIG. 23, insert), overlaps with the platinum oxidation characteristic during faster scans. This is an indication of insufficient electrolyte conductivity for larger currents or faster scan rates. Thus, slower sweep rates that allow slower reactions to proceed in real time equilibrium conditions are preferred.

The electrode potential at which reduction and chemisorption of $CO_2$ occurs affects the reaction kinetics of those processes, and thus, accumulation of surface $CO_2$ species. Conditions that allow $CO_2$ to adsorb exclusively in the form of surface bonded CO with the highest efficiency are preferred. The choice of platinum also helps the efficiency of surface CO formation, and the addition of gold adatoms increases the efficiency even further.

Figure 24:
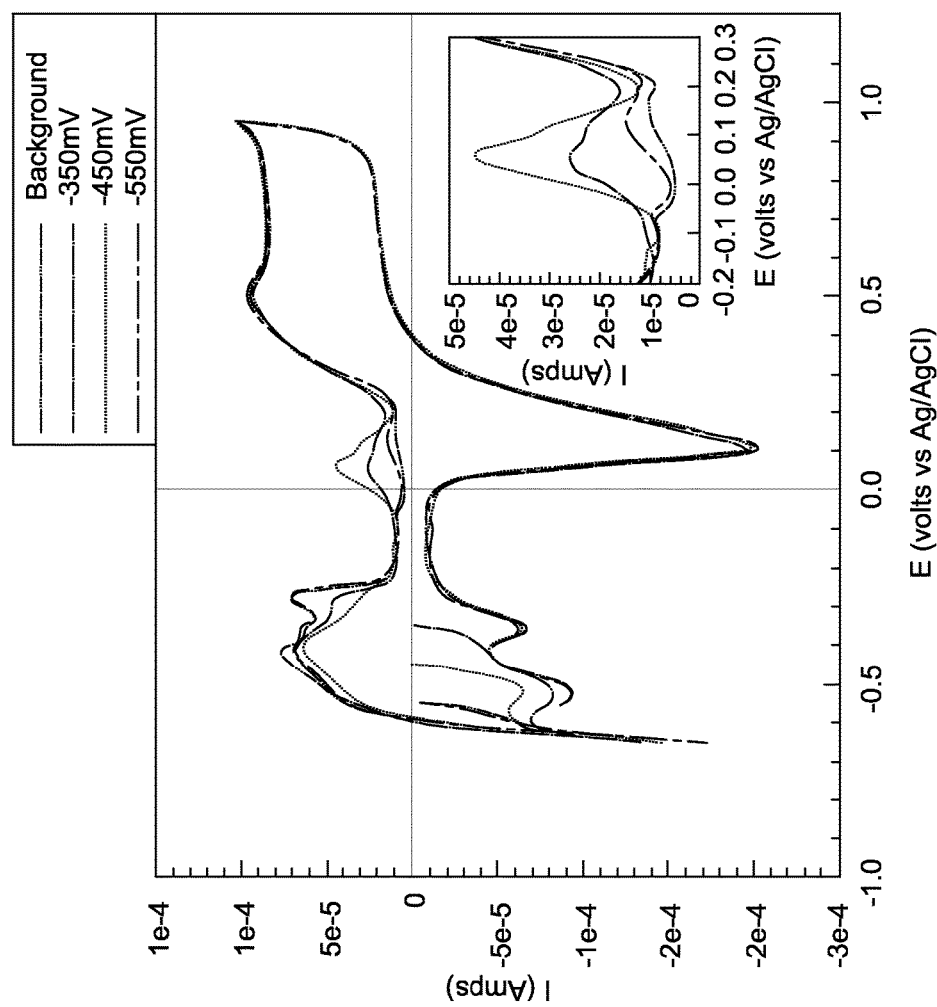
FIG. 24 shows the cyclic voltammetry of a flow-through embodiment of a $CO_2$ sensor in 0.1M $H_2SO_4$ after applying cathodic step at different potentials.
Figure 25:
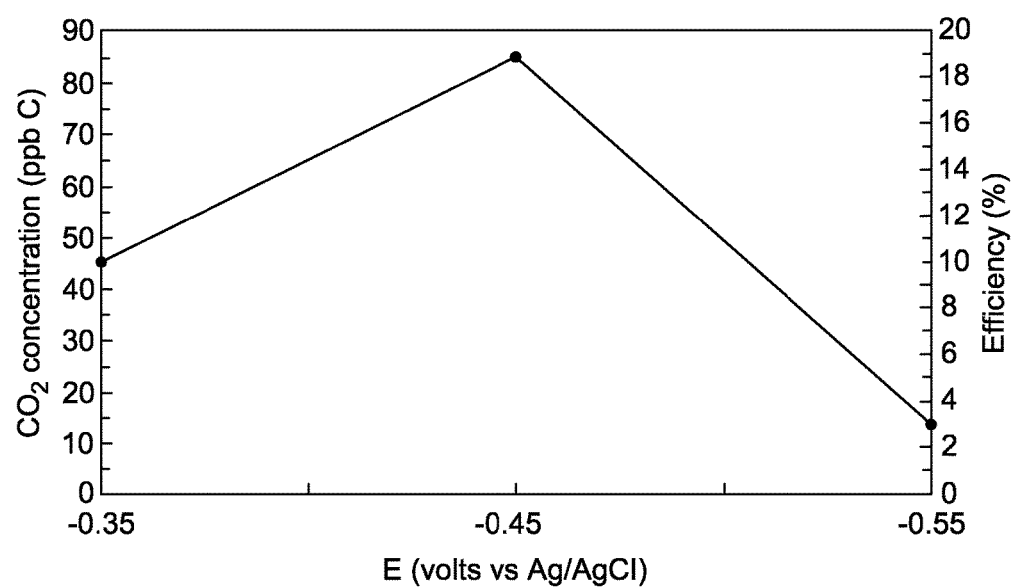
FIG. 25 is the $CO_2$ sensor response to 450 ppb C carbon dioxide as a function of adsorption potential.

FIG. 24 shows the response of an online $CO_2$ sensor in a 0.1 M $H_2SO_4$ solution with 450 ppb C $CO_2$. The solution flow rate was 133 μl/min. The potential sweep rate was 10 mV/sec. An adsorption process was conducted in potentials of −350 mV, −450 mV, and −550 mV (vs. Ag/AgCl). The adsorption time was 10 min. Oxidation peaks are presented in FIG. 24 and their numerical values are in FIG. 25. The insert in FIG. 24 is an enlarged view of the stripping current peak. At a potential of −450 mV, the maximum efficiency occurs. The effective $CO_2$ recovery is close to 20%.

Figure 26:
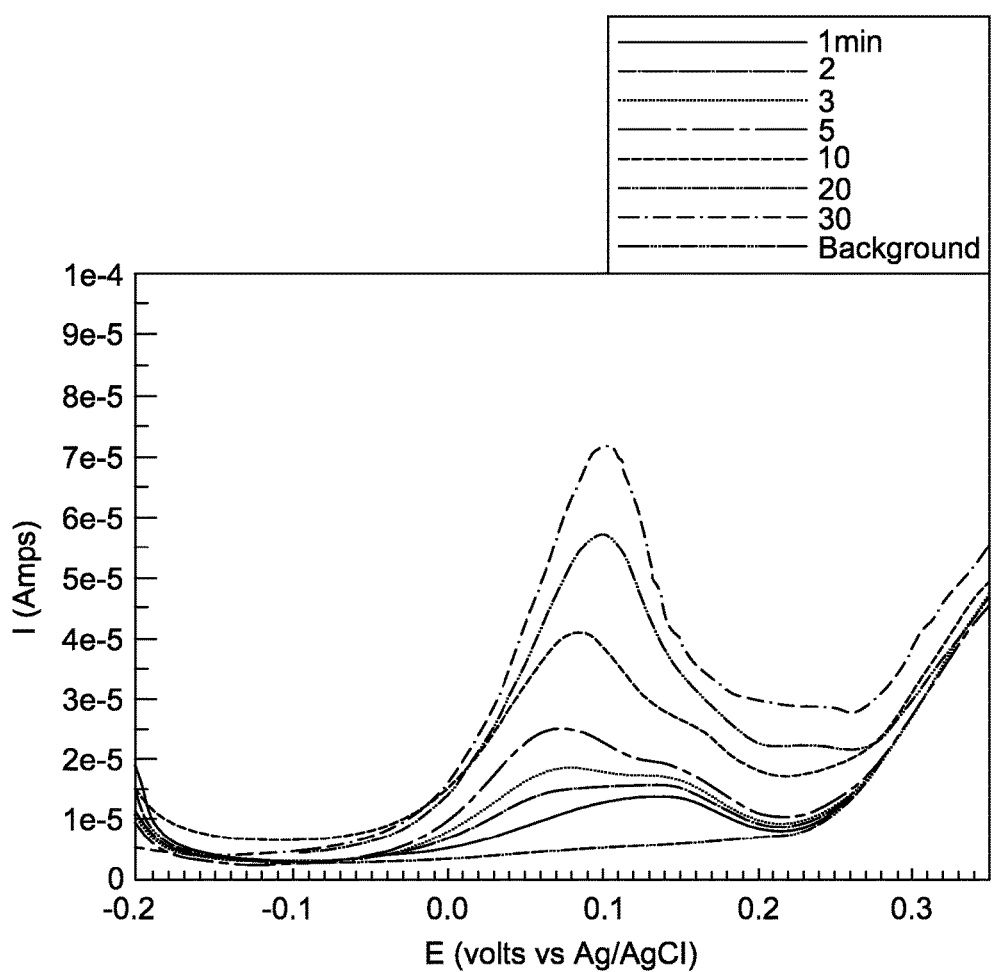
FIG. 26 shows the anodic stripping peak of a flow-through embodiment of a $CO_2$ sensor as a function of adsorption time at a sample $CO_2$ concentration of 100 ppb C.

The $CO_2$ signal is also affected by adsorption time. The efficiency of collection of the $CO_2$ derived species as a function of adsorption time is presented in FIG. 26. A 0.1 M $H_2SO_4$ solution with a $CO_2$ concentration of 100 ppb C was chosen for these experiments. The solution flow rate through the sensor was 130 μl/min. The potential sweep rate was 10 mV/sec and the adsorption potential was −450 mV vs. Ag/AgCl.

Figure 27:
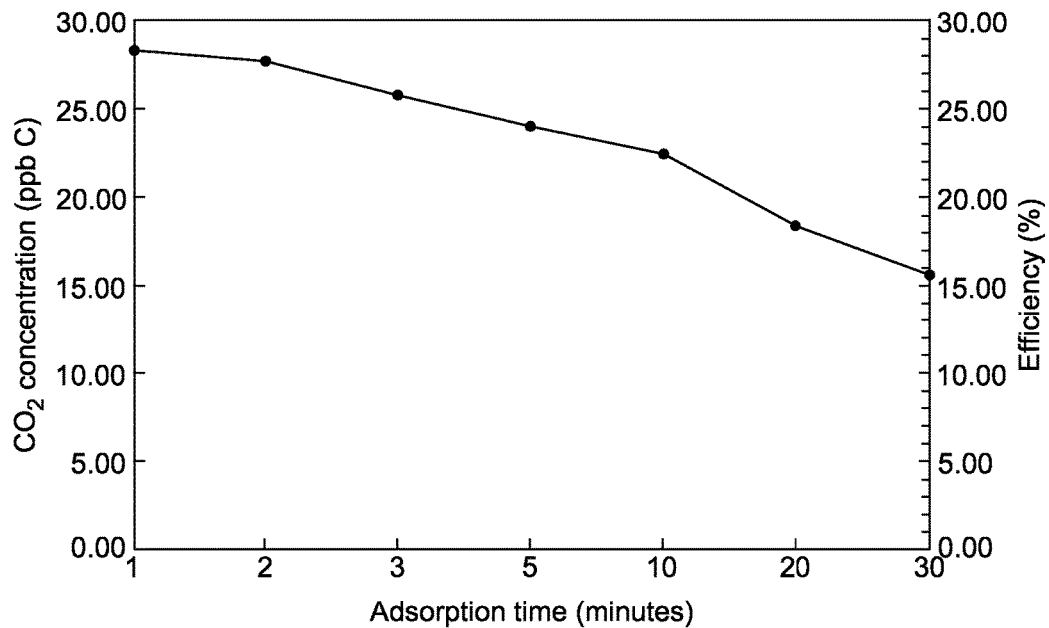
FIG. 27 shows the $CO_2$ collection efficiency as a function of adsorption time at a sample $CO_2$ concentration of 100 ppb C.
Figure 28:
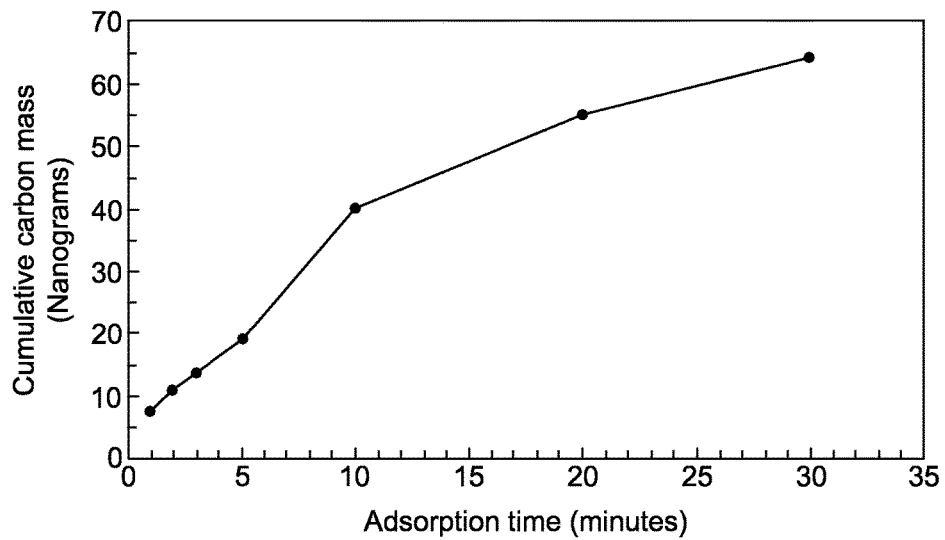
FIG. 28 shows the kinetics of $CO_2$ adsorption, at a sample $CO_2$ concentration of 100 ppb C.

The efficiency of $CO_2$ collection is at its maximum for the shortest times investigated. It is close to 30% for 1 minute adsorption and then decreases with increasing adsorption time. This trend is illustrated in FIG. 27 which shows the $CO_2$ collection efficiency as a function of adsorption time in a 0.1 M $H_2SO_4$ solution with a $CO_2$ concentration of 100 ppb C. With the sensor active volume of 360 μl and the sample flow rate at 130 μl/min, the sample residence time at the sensor is less than 3 minutes. Hence, the decrease in collection efficiency is not related to sample diffusion problems, but to the electrode's energy heterogeneity. The activity towards adsorbing $CO_2$ species decreases with surface coverage with chemisorbed $CO_2$. The kinetic effects of a decreasing available electrode surface are shown in FIG. 28.

Figure 29:
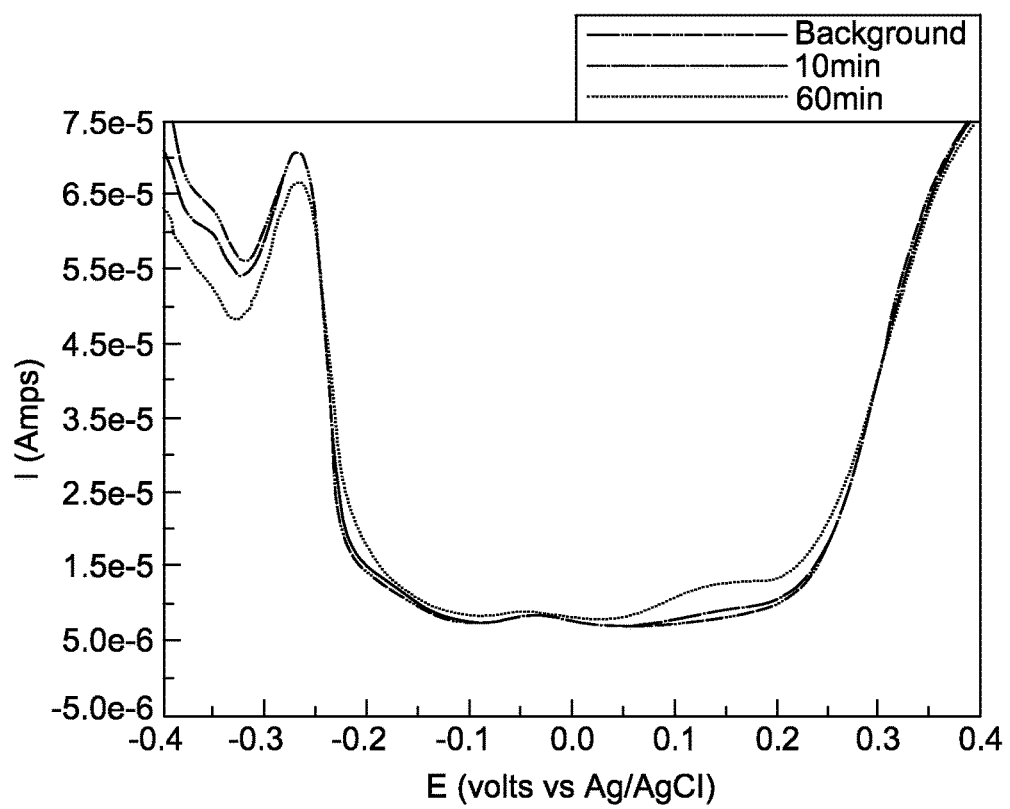
FIG. 29 shows the anodic stripping peak of a flow-through embodiment of a $CO_2$ sensor as a function of adsorption time at a sample $CO_2$ concentration of 18 ppb C.

The $CO_2$ kinetic detection limit is shown in FIG. 29. Adsorption of a low concentrated $CO_2$ solution, 18 ppb C in the given graph, is barely detectable on the stripping voltammogram after 10 minutes. However, after 1 hour of adsorption, $CO_{ads}$ accumulation reached a detectable level.

Figure 30:
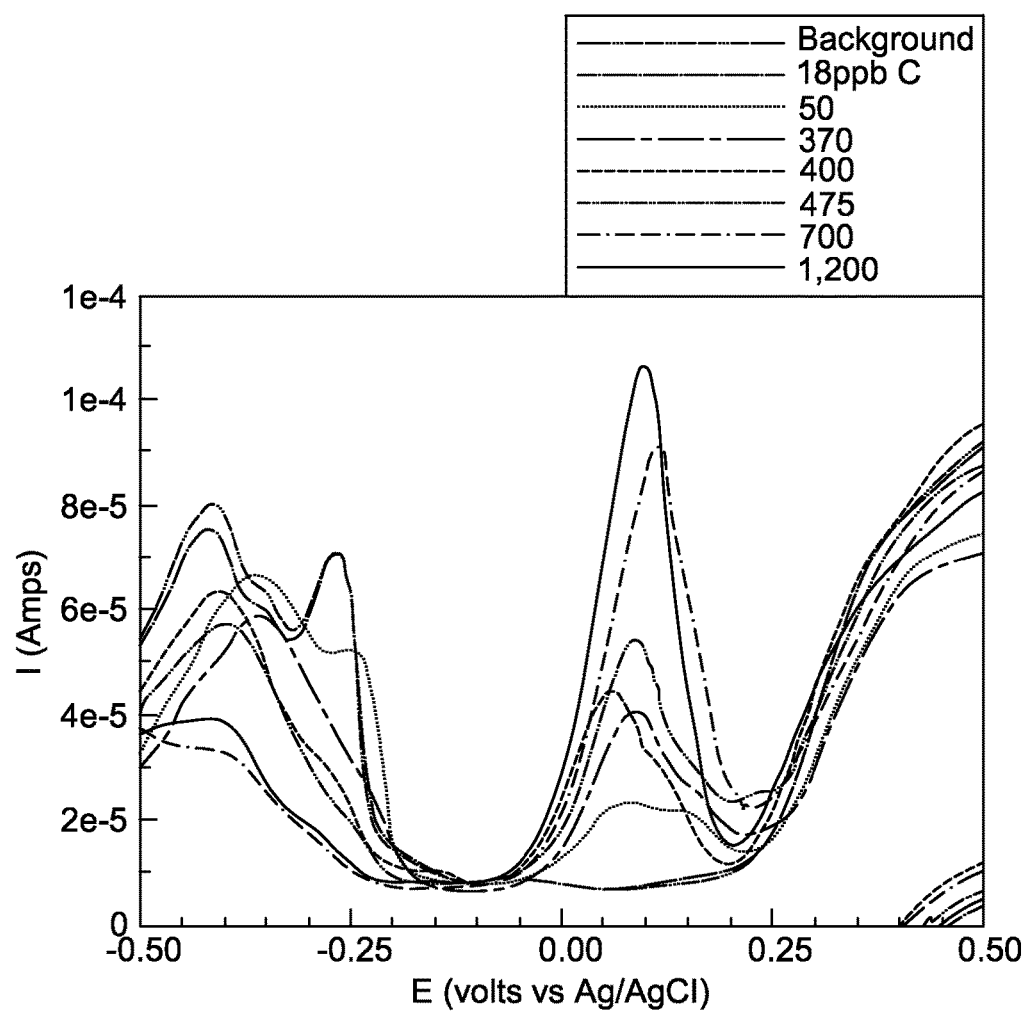
FIG. 30 shows the anodic stripping peak of a $CO_2$ sensor as a function of sample $CO_2$ concentration.
Figure 31:
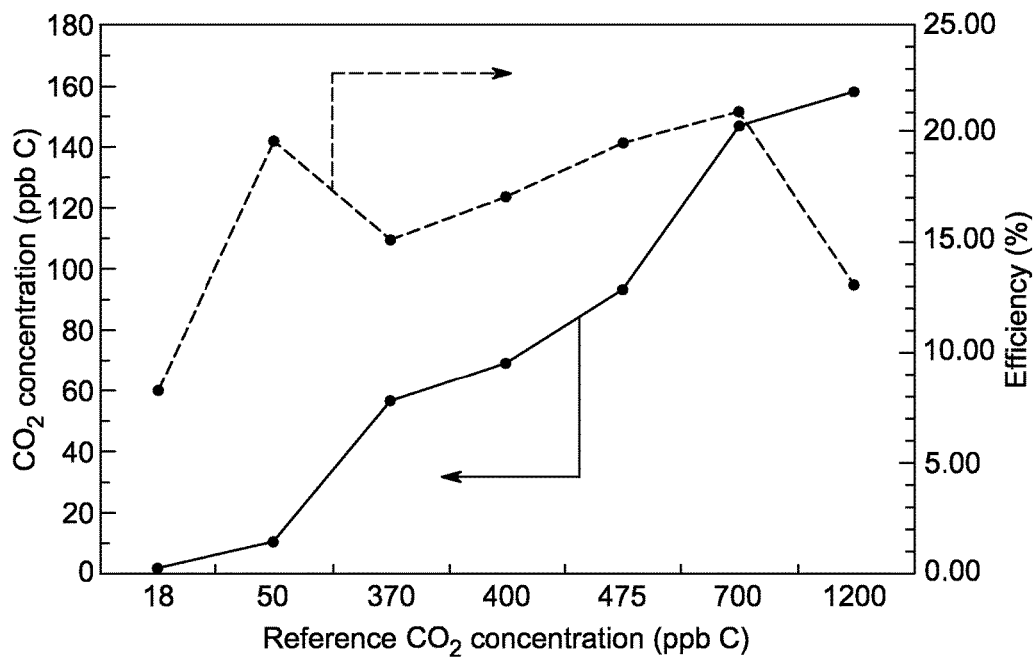
FIG. 31 shows the $CO_2$ collection efficiency as a function of sample $CO_2$ concentration.

Sensor response to different $CO_2$ levels in the sample is shown in FIG. 30. The solution was a 0.1 M $H_2SO_4$ solution with a flow rate through the sensor of 40 μl/min. The potential sweep rate was 10 mV/sec and the adsorption potential was −450 mV. The adsorption time was 10 minutes. The efficiency is close to 20% in most cases (FIG. 31). The exceptions are the lowest and highest concentrations.

Figure 32:
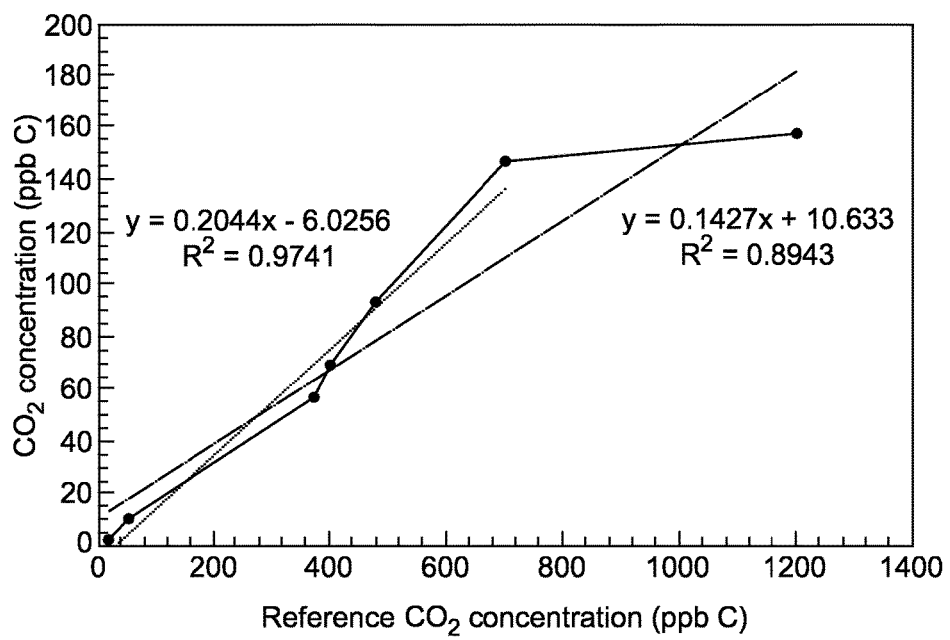
FIG. 32 shows various calibration curves of an embodiment of a $CO_2$ sensor.

The data point for the lowest concentration may have a detection limit error, and likely not very reliable. For the highest concentration, the problem may be due to the electrode changing activity (as discussed previously). FIG. 32 shows various linear calibration curves for the sensor. The dashed line ($R^2=0.8943$) is based on all the data points, whereas the data point for the highest $CO_2$ concentration was eliminated for the dotted line ($R^2=0.9741$). Linearity may be improved by varying the adsorption times across the full detection range.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. For example, the patentable scope of the invention is not limited to the various cell and TOC analyzer configurations disclosed in the examples.

What is claimed is:

1. A method for measuring carbon dioxide in an aqueous stream, said method comprising:
   providing said aqueous stream, wherein any organic carbon in said aqueous stream has been oxidized therein;
   providing a carbon dioxide measurement module comprising at least one platinum electrode therein;
   contacting said aqueous stream with said platinum electrode;
   applying a cathodic potential to said platinum electrode;
   applying an anodic potential to said platinum electrode and measuring the amperometric response of said platinum electrode while maintaining contact of said platinum electrode with said aqueous stream; and
   equating said amperometric response to a total organic carbon content of said aqueous stream.

2. The method of claim 1, wherein said anodic potential is an anodic potential sweep or an anodic potential step.

3. The method of claim 1, wherein said platinum electrode is platinized.

4. The method of claim 1, wherein said platinum electrode is decorated with gold adatoms.

5. The method of claim 1, wherein said organic carbon in said aqueous stream has been oxidized using at least one method selected from the group consisting of electrooxidation, chemical oxidation, UV-persulfate oxidation, thermal oxidation, and catalytic oxidation.

6. The method of claim 1, wherein said method further comprises adding an electrolyte to said aqueous stream before applying said cathodic potential.

7. The method of claim 6, wherein said electrolyte is an acid.

8. The method of claim 7, wherein said acid is sulfuric acid.

9. A method for measuring total organic carbon in an aqueous stream, said method comprising:
   providing said aqueous stream;
   providing an oxidation module comprising at least one doped diamond electrode therein;
   providing a carbon dioxide measurement module comprising at least one platinum electrode therein;
   contacting said aqueous stream with said doped diamond electrode in said oxidation module and applying an oxidizing potential to said doped diamond electrode to oxidize any organics in said aqueous stream, thereby forming an oxidized aqueous stream;
   transferring said oxidized aqueous stream from said oxidation module to said carbon dioxide measurement module;
   contacting said oxidized aqueous stream with said platinum electrode in said carbon dioxide measurement module and applying a cathodic potential to said platinum electrode and thereafter applying an anodic potential to said platinum electrode and measuring an amperometric response of said platinum electrode; and
   equating said amperometric response of said platinum electrode to a total organic content of said aqueous stream.

10. The method of claim 9, wherein said platinum electrode is platinized.

11. The method of claim 9, wherein said platinum electrode is decorated with gold adatoms.

12. The method of claim 9, wherein said doped diamond electrode is a boron-doped diamond electrode.

13. The method of claim 9, wherein said method further comprises adding an electrolyte to either said aqueous stream before applying said oxidation potential, or to said oxidized aqueous stream before applying said cathodic potential.

14. The method of claim 13, wherein said electrolyte is an acid.

15. The method of claim 14, wherein said acid is sulfuric acid.

16. The method of claim 9, wherein said anodic potential is an anodic potential sweep or an anodic potential step.

17. The method of claim 9, wherein said oxidizing potential is selected from the group consisting of a static anodic potential, an alternating potential waveform, or anodic potential pulses.

18. An apparatus for oxidizing organics in an aqueous stream, said apparatus comprising:
   an oxidation module comprising a dual-compartment cell, wherein said dual-compartment cell has a first compartment with a doped diamond anode therein and a second compartment with a cathode therein;
   and wherein said oxidation module is configured to contact said aqueous stream with said doped diamond anode and to apply an oxidizing potential to said doped diamond anode, thereby oxidizing any organics in said aqueous stream to form an oxidized aqueous stream.

19. The apparatus of claim 18, wherein said dual-compartment cell further comprises a conducting membrane separating said first compartment from said second compartment.

20. The apparatus of claim 19, wherein said conducting membrane is a proton exchange membrane.

21. The apparatus of claim 18, wherein said oxidizing potential is selected from the group consisting of a static anodic potential, an alternating potential waveform, or anodic potential pulses.

22. The apparatus of claim 18, wherein said doped diamond anode is a boron-doped diamond anode.

23. An apparatus for measuring total organic carbon in an aqueous stream, said apparatus comprising:
   an oxidation module comprising at least one doped diamond electrode therein, said oxidation module configured to contact said aqueous stream with said doped diamond electrode and to apply an oxidizing potential to said doped diamond electrode, thereby oxidizing any organics in said aqueous stream to form an oxidized aqueous stream;
   a carbon dioxide measurement module comprising at least one platinum electrode therein, said carbon dioxide measurement module configured to contact said oxidized aqueous stream with said platinum electrode and to apply a cathodic potential to said platinum electrode and thereafter apply an anodic potential to said platinum electrode;
   a fluid transfer module operatively connected to said oxidation module and said carbon dioxide measurement module, said fluid transfer module configured to transfer said oxidized aqueous stream from said oxidation module to said carbon dioxide measurement module; and a control module operatively connected to said carbon dioxide measurement module, said control module configured to measure an amperometric response of said platinum electrode and equate said amperometric response to a total organic content of said aqueous stream.

24. The apparatus of claim 23, wherein said control module is further operatively connected to said oxidation module and said fluid transfer module.

25. The apparatus of claim 23, wherein said platinum electrode is platinized.

26. The apparatus of claim 22, wherein said platinum electrode is decorated with gold adatoms.

27. The apparatus of claim 23, wherein said doped diamond electrode is a boron-doped diamond electrode.

28. The apparatus of claim 23, wherein said anodic potential is an anodic potential sweep or an anodic potential step.

29. The apparatus of claim 23, wherein said oxidizing potential is selected from the group consisting of a static anodic potential, an alternating potential waveform, or anodic potential pulses.

30. The apparatus of claim 23, wherein said oxidation module further comprises a dual-compartment cell wherein said dual-compartment cell has a first compartment with an anode therein and a second compartment with a cathode therein.

31. The apparatus of claim 30, wherein said dual-compartment cell further comprises a conducting membrane separating said first compartment from said second compartment.

32. The apparatus of claim 31, wherein said conducting membrane is a proton exchange membrane.

33. A system for measuring carbon dioxide in an aqueous stream, said system comprising:
    a memory; and
    a processor operatively connected to said memory, said processor configured to:
        receive inputs, said inputs comprising an amperometric response to an aqueous stream, wherein said amperometric response was generated by:
            contacting said aqueous stream with said platinum electrode:
            applying a cathodic potential to said platinum electrode; and
            applying an anodic potential to said platinum electrode and measuring said amperometric response of said platinum electrode;
        use said inputs to calculate outputs, said outputs comprising a total organic carbon content of said aqueous stream; and
        store said outputs in said memory,
        wherein said platinum electrode is decorated with gold adatoms.

34. The system of claim 33, wherein said inputs further comprise a background amperometric response.

35. A non-transitory computer readable medium with computer executable instructions stored thereon executed by a processor to perform a method of measuring total organic carbon in an aqueous stream, the method comprising:
    applying a cathodic potential to a platinum electrode contacting said aqueous stream;
    applying an anodic potential to said platinum electrode;
    measuring said amperometric response of said platinum electrode;
    calculating a total organic carbon content of said aqueous stream using said measured amperometric response; and
    storing said calculated total organic carbon content in said memory.

36. The medium of claim 35, wherein said method further comprises measuring a background amperometric response, wherein said total organic carbon content of said aqueous stream is calculated using said measured amperometric response and said measured background amperometric response.

37. The medium of claim 35, wherein said platinum electrode is platinized.

38. The medium of claim 35, wherein said platinum electrode is decorated with gold adatoms.

* * * * *